US007662609B2

(12) United States Patent
Humphreys et al.

(10) Patent No.: US 7,662,609 B2
(45) Date of Patent: Feb. 16, 2010

(54) ***E.COLI* HOST CELLS WITH MODIFIED PHOS/PSTS PERIPLASMIC PHOSPHATE-BINDING PROTEINS, AND METHOD OF MANUFACTURING RECOMBINANT FABS**

(75) Inventors: David Paul Humphreys, Maidenhead (GB); Andrew Paul Chapman, Hampton (GB); Martyn Kim Robinson, High Wycombe (GB); Mariangela Spitali, Maidenhead (GB)

(73) Assignee: UCB Pharma S.A., Brussels (BE)

( * ) Notice: Subject to any disclaimer, the term of this patent is extended or adjusted under 35 U.S.C. 154(b) by 114 days.

(21) Appl. No.: 10/531,402

(22) PCT Filed: Oct. 15, 2003

(86) PCT No.: PCT/GB03/04474

§ 371 (c)(1),
(2), (4) Date: Oct. 11, 2005

(87) PCT Pub. No.: WO2004/035792

PCT Pub. Date: Apr. 29, 2004

(65) Prior Publication Data

US 2007/0054354 A1    Mar. 8, 2007

(30) Foreign Application Priority Data

Oct. 16, 2002    (GB) ................... 0224082.8

(51) Int. Cl.
*C12N 1/21* (2006.01)
*C12N 15/13* (2006.01)

(52) U.S. Cl. ................ 435/252.33; 435/69.1
(58) Field of Classification Search ............ None
See application file for complete search history.

(56) References Cited

U.S. PATENT DOCUMENTS

| 4,532,207 A | 7/1985 | Brewer et al. ......... 435/68 |
| 5,304,472 A | 4/1994 | Bass et al. ........... 435/69.1 |
| 5,783,423 A | 7/1998 | Wood et al. ......... 435/69.6 |

FOREIGN PATENT DOCUMENTS

| EP | 737 747 A2 | 10/1996 |
| GB | 224082 | 11/1924 |
| WO | WO 98/18946 A1 | 5/1998 |
| WO | WO 00/61725 A1 | 10/2000 |
| WO | WO 2004/031188 A1 | 4/2004 |
| WO | WO 2004/035792 A1 | 4/2004 |

OTHER PUBLICATIONS

Shuman, J. Biol. Chem. 257(10), 5455-5461, 1982.*
Amemura, M., et al., "Cloning of and complementation tests with alkaline phosphatase regulatory genes (*phoS* and *phoT*) of *Escherichia coli*," *J. of Bacteriology*, 1982, 152(2), 692-701.
Blattner, F.R., et al., "The complete genome sequence of *Escherichia coli* K-12," *Science*, 1997, 277, 1453-1462.
Blomfield, I.C., et al., "Allelic exchange in *Escherichia coli* using the *Bacillus subtilis sacB* gene and a temperature-sensitive pSC101 replicon," *Molecular Microbiology*, 1991, 5(6), 1447-1457.
Carrier, A., et al., "recombinant antibody-alkaline phosphatase conjugates for diagnosis of human IgGs: application to anti-HBsAg detection," *J. of Immunological Methods*, 1995, 181, 177-186.
Collins-Racie, L.A., et al., "Production of recombinant bovine enterokinase catalytic subunit in *Escherichia coli* using the novel secretory fusion partner DsbA," *Bio/Technology*, 1995, 13, 982-987.
Cunningham, B.C., et al., "High-resolution epitope mapping of hGH-Receptor interations by alanine-scanning mutagenesis," *Science*, 1989, 244, 1081-1085.
Dalbøge, H., et al., "A novel enzymatic method for production of authentic hGH from an *Escherichia coli* produced hGH-precursor," *Bio/Technology*, 1987, 5, 161-164.
di Guan, C., et al., "Vectors that facilitate the expression and purification of foreign peptides in *Escherichia coli*, by fusion to maltose-binding protein," *Gene*, 1988, 67, 21-30.
Egmond, M.R., et al., "Engineering surface charges in a subtilisin," in *Subtilisin Enzymes: Practical protein Engineering*, Bott, R., et al.(Eds.), 1996, 219-228.
Gräslund, T., et al., "Strategy for highly selective ion-exchange capture using a charge-polarizing fusion partner," *J. of Chromatography A*, 2002, 942, 157-166.
Gräslund, T., et al., "Charge engineering of a protein domain to allow efficient ion-exchange recovery," *Protein Engineering*, 2000, 13(10), 703-709.
Hamilton, C.M., et al., "New method for generating deletions and gene replacements in *Escherichia coli*," *J. of Bacteriology*, 1989, 171(9), 4617-1622.
Humphreys, D.P., et al., "Therapeutic antibody production technologies: molecules, applications, expression and purification," *Current Opinion in Drug Discovery and Development*, 2001, 4(2), 172-185.
Jonasson, P., et al., "Genetic design for facilitated production and recovery of recombinant proteins in *Escherichia coli*," *Biotechnology & Applied Biochemistry*, England, 2002, 35, 91-105.
Link, A.J., et al., "Methods for generating precise deletions and insertions in the genome of wild-type *Escherichia coli*: application to open reading frame characterization," *J. of Bacteriology*, 1997, 179(20), 6228-6237.
Luecke, H., et al., "High specificity of a phosphate transport protein determined by hydrogen bonds," *Nature*, 1990, 347, 402-406.
Marttila, A.T., et al., "Engineering of chicken avidin: a progressive series of reduced charge mutants," *FEBS Letts.*, 1998, 441, 313-317.
Meyer, D.E., et al., "Purification of recombinant proteins by fusion with thermally-responsive polypeptides," *Nature Biotechnology*, 1999, 17, 1112-1115.
Mhatre, R., et al., "Purification of antibody Fab fragments by cation-exchange chromatography and pH gradient elution," *J. of Chromatography A*, 1995, 707, 225-231.

(Continued)

*Primary Examiner*—Nancy Vogel
(74) *Attorney, Agent, or Firm*—McDonnell Boehnen Hulbert & Berghoff LLP

(57) ABSTRACT

The present invention provides an *Ecoli* host cell expressing a recombinant antibody characterized in that the *Ecoli* host cell has been genetically modified in order to change at least one physical property of one or more *Ecoli* proteins which in the wild type copurify with said recombinant antibody.

7 Claims, 14 Drawing Sheets

OTHER PUBLICATIONS

Niederauer, M.Q., et al., "Characterization and polyelectrolyte of β-galactosidase containing genetic fusions of charged polypeptides," *Biotechnology Progress*, 1994, 10, 237-245.

Nielsen, O.J., et al., "Erythropoietin-β-D-galactosidase: the generation, purification and use of a fusion protein," *J. of Immunological Methods*, 1988, 111, 1-9.

O'Brien, P.M., et al., "Bacterial expression and purification of recombinant," *Protein Expression & Purification*, 2002, 24, 43-50.

Ong, E., et al., "Enzyme immobilization using the cellulose-binding domain of a *Cellulomonas fimi* exoglucanase," *Bio/Technology*, 1989, 7, 604-607.

Persson, M., et al., "Enzyme purification by genetically attached polycysteine and polyphenylalanine affinity tails," *Analytical Biochemistry*, 1988, 172, 330-337.

Plückthun, A., et al., "New protein engineering approaches to multivalent and bispecific antibody fragments," *Immunotechnology*, 1997, 3, 83-105.

Sassenfeld, H.M., et al., "A polypeptide fusion designed for the purification of recombinant proteins," *Bio/technology*, 1984, 2, 76-81.

Sassenfeld, H.M., "Engineering proteins for purification," *Tibtech*, 1990, 8, 88-93.

Smith, D.B., et al., "Single-step purification of polypeptides expressed in *Escherichia coli* as fusions with glutathione S-transferase," *Gene*, 1988, 67, 31-40.

Stempfer, G., et al., "Improved refolding of an immobilized fusion protein," *Nature Biotechnology*, 1996, 14, 329-334.

Verma, R., et al., "Antibody engineering: comparison of bacterial, yeast, insect and mammalian expression system," *J. of Immunological Methods*, 1998, 216, 165-181.

Zoller, M.J., et al., "Oligonucleotide-directed mutagenesis using M13-derived vectors: an efficient and general procedure for the production of point mutations in any fragment of DNA," *Nucleic Acid Res.*, 1982, 10(20), 6487-6500.

* cited by examiner

Anti-PhoS        Anti-Fd

Anti-PhoS

Anti-Fd

E.COLI HOST CELLS WITH MODIFIED PHOS/PSTS PERIPLASMIC PHOSPHATE-BINDING PROTEINS, AND METHOD OF MANUFACTURING RECOMBINANT FABS

The present invention relates to E. coli host cells for use in the expression of recombinant proteins and more specifically provides improved E. coli host cells for the manufacture of recombinant antibodies.

The large-scale, economic purification of recombinant proteins is increasingly an important problem for the biotechnology industry. Generally, recombinant proteins are manufactured using either mammalian or bacterial cell lines engineered to produce the protein of interest by insertion of a recombinant plasmid containing the gene for that protein. Proteins are either secreted directly from the cell into the surrounding growth media or they are made intracellularly. For the latter proteins, the first step of a purification process involves lysis or disruption of the cell, which can be done by a variety of methods, including mechanical shear, osmotic shock, or enzymatic treatments. Such disruption releases the contents of the cell into the homogenate, and in addition produces subcellular fragments that are generally removed by differential centrifugation or by filtration. The same problem arises, although on a smaller scale, with directly secreted proteins due to the natural death of cells and release of intracellular host cell proteins in the course of the protein production run. Recombinant proteins produced in this way need to be purified away from contaminating host cell proteins, as they, may be toxic or immunogenic. High purity is essential for recombinant proteins required for therapeutic use such as antibodies.

Antibodies and antibody fragments until recently were usually manufactured in mammalian cells, but alternative production systems such as E. coli, Pichia yeasts and plants have also been used. These manufacturing alternatives have been driven by the specific antibody product and the balance between scale, cost, speed, capital risk and biological safety (Humphreys and Glover, 2001, Current Opinion in Drug Discovery and Development, 4, 172-185). In addition to the more obvious costs of fermentation plant, operator time, media ingredients and process turnaround/capital depreciation, there are significant costs associated with 'downstream processing' i.e. crude product storage, handling and purification.

Large-scale antibody purification relies predominantly on fractional precipitation, ion exchange, size exclusion and hydrophobic interaction chromatography because these methods are cost efficient and physically robust. If purification cannot be achieved using these methods then considerable development will be required to scale up more expensive analytical methods such as affinity chromatography. This problem is likely to arise when contaminating host proteins have similar physical properties to the recombinant antibody, such as pi, size or hydrophobicity. Removal of these contaminants may require specialist purification steps that are highly undesirable when performed on a large-scale. Hence there is a need to improve and simplify large-scale purification processes for recombinantly manufactured antibodies where contaminating host proteins are a particular problem.

The present invention solves the problem described above by providing improved E. coli host cells for the manufacture of recombinant antibodies. More particularly, the present invention provides E. coli host cells for the production of recombinant antibodies, characterised in that said cells have been genetically modified in order to change at least one physical property of one or more E. coli proteins which in the wild type co-purify with said recombinant antibody.

Accordingly, we have been able to demonstrate that the purification process for antibodies produced in E. coli can be improved by altering the physical properties of selected E. coli proteins so they no longer co-purify with the recombinant antibody. As a result of using the E. coli host cells of the present invention it is possible to improve the purification process for antibodies produced using said cells, for example the process may be quicker and/or more economical than for those produced in wild type E. coli. Therefore, improvements in the purification of an antibody in the present invention may be considered to be any advantageous alteration to a purification process resulting from modifications in the physical properties of E. coli host proteins. Improvements may include but are not limited to improvements in speed of purification, reduction in purification costs or increase in quality of antibody produced. In one embodiment of the present invention the purification process for a recombinant antibody is improved by the removal of an entire purification step resulting in both cost and time savings. Preferably the step that is removed is an affinity chromatography step, an ion exchange step, a size exclusion step or a hydrophobic interaction step. In a preferred embodiment the step that is removed during the purification of an antibody Fab' fragment is a hydrophobic interaction step and the E. coli protein that is altered is the Phosphate binding protein (PhoS/PstS). Preferably removal of said step leads to cost savings of approximately 15% compared to the original purification process on a molar Fab' basis.

In another embodiment of the present invention, the purification process for recombinant antibodies produced in the host cells of the present invention is improved by reducing the amount of column matrix required, hence reducing material costs and process times. Preferably this is achieved by reducing the number of contaminating host proteins which normally co-purify with the recombinant antibody and reduce the capacity of the column to bind antibody. In a preferred embodiment the column capacity that is increased is a cation exchange column and the E. coli host proteins that are altered to prevent binding to that column are Dipeptide binding protein (DppA), Maltose binding protein (MBP) and Thioredoxin.

Thus according to the present invention there are provided improved E. coli host cells for the manufacture of recombinant antibodies. The E. coli host cells of the present invention may be naturally occurring organisms or mutated organisms capable of producing recombinant antibodies. Preferably, however, the host organism is an organism or the progeny of an organism which has been transformed using recombinant DNA techniques with a heterologous DNA sequence which codes for the production of a recombinant antibody. Specific host E. coli strains suitable for use in the present invention include but are not limited to MC4100, TG1, TG2,. DHB4, DH5α, DH1, BL21, XL1Blue. One preferred E. coli host is E. coli W3110 (ATCC 27,325) a commonly used host strain for recombinant protein fermentations. Expression of any foreign gene in E. coli is achieved by insertion of a cDNA copy of the gene into an expression vector. Many forms of expression vector are available. Such vectors usually comprise a plasmid. origin of DNA replication, an antibiotic selectable marker and a promoter and transcriptional terminator separated by a multi-cloning site (expression cassette) and a DNA sequence encoding a ribosome binding site.

The term 'wild type' refers to the host cell in which a contaminating host protein has not been modified. It is possible that other proteins in this host cell have been modified for purposes outside this invention.

The *E. coli* host proteins selected for genetic modification are proteins that in the wild type are known to co-purify with the recombinant antibody during purification. The term 'co-purify' refers to the purification of one protein with another under the same set of purification conditions. Typically this refers to the purification of contaminating *E. coli* proteins along with a recombinantly expressed antibody during purification processes such as chromatography.

The term 'genetic modification' refers to one or more deletion, insertion, substitution or mutation of a gene sequence resulting in a change in the physical properties of the protein encoded by that gene. Preferably these changes do not affect the physiological or biological activity of the encoded protein.

The term 'hydrophobicity' refers to the net effect of hydrophobic and hydrophilic amino acids over a whole protein surface, or in localised surface patches, on solubility of the protein in water or organic solvents and its interaction with solid surfaces and matrices.

The terms 'pl or isoelectric point' refer to the pH at which the polypeptide's positive charge balances its negative charge. pl can be calculated from the net charge of the amino acid residues of the polypeptide or can be determined by isoelectric focusing The term 'physical property' refers to the physical nature of the protein itself rather than its physiological or biological activity. Preferably, physical property refers to characteristics of the protein such as size, hydrophobicity and isoelectric point. Which physical property of the *E. coli* host protein is altered will be dictated by the purification process for the recombinant antibody and the improvements that are required. For example, the isoelectric point of a protein may be altered to prevent it binding to a particular ion exchange column under certain conditions.

The physical properties of contaminating *E. coli* proteins that are altered by genetic modification can include, but are not limited to, isoelectric point and/or size and/or hydrophobicity. The size of the protein refers to the molecular weight of the protein. Alterations to the physical properties of the contaminating proteins can be made using any combination of addition, deletion, substitution or insertion of specific sequences within the encoding nucleotide sequence. In one embodiment the physical properties of the protein are altered by the addition or deletion of at least one amino acid at the N or C terminus. In one embodiment a physical property of a contaminating host protein is altered by the addition of an amino acid tag to the C-terminus. In a preferred embodiment the physical property that is altered is the isoelectric point and the amino acid tag is a poly-aspartic acid tag attached to the C-terminus. In one embodiment the *E. coli* proteins altered by the addition of said tag are Dipeptide binding protein (DppA), Maltose binding protein (MBP), Thioredoxin and Phosphate binding protein (PhoS/PstS). In one specific embodiment the pl of the *E. coli* Phosphate binding protein (PhoS/PstS) is reduced from 7.2 to 5.1 by the addition of a poly-aspartic acid tag (polyD), containing 6 aspartic acid residues to the C-terminus.

Also preferred is the modification of specific residues of the contaminating *E. coli* protein to alter its physical properties, either alone or in combination with the addition of N or C terminal tags. Such changes can include insertions or deletions to alter the size of the protein or amino acid substitutions to alter pl or hydrophobicity. In one embodiment these residues are located on the surface of the protein. In a preferred embodiment surface residues of the PhoS protein are altered in order to reduce the pl of the protein. Preferably residues that have been implicated to be important in phosphate binding (Bass, U.S. Pat. No. 5,304,472) are avoided in order to maintain a functional PhoS protein. Preferably lysine residues that project far out of the surface of the protein or are in or near large groups of basic residues are targeted. In one embodiment, the PhoS protein has a hexa poly-aspartic acid tag attached to the C-terminus whilst surface residues at the opposite end of the molecule are targeted for substitution. Preferably selected lysine residues are substituted for glutamic acid or aspartic acid to confer a greater potential pl change than when changing neutral residues to acidic ones. The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid. In preferred mutations of PhoS in the present invention lysine residues (K) 275, 107, 109, 110, 262, 265, 266, 309, 313 are substituted for glutamic acid (E), as single or combined mutations, in addition lysine(K)318 may be substituted for aspartic acid (D) as a single or combined mutation. Preferably the single mutations are K262E, K265E and K266E. Preferably the combined mutations are K265/266E and K110/265/266E. More preferably, all mutations are combined with the polyaspartic acid (polyD) tag attached at the C-terminus and optionally also with the K318D substitution. In a preferred embodiment the mutations result in a reduction in pl of at least 2 units. Preferably the mutations of the present invention reduce the pl of PhoS from 7.2 to between about 4 and about 5.5. In one embodiment of the present invention the pl of the PhoS protein of *E. coli* is reduced from 7.2 to about 4.9, about 4.8 and about 4.5 using the mutations polyD K318D, polyD K265/266E and polyD K110/265/266E respectively.

Preferably all genetic modifications of *E. coli* host proteins result in proteins which no longer co-purify with the recombinant antibody during the desired purification step. Preferably alterations to the PhoS protein result in a protein which does not co-purify on ion exchange with an antibody Fab' fragment and preferably a previously required hydrophobic interaction step is no longer necessary. Preferably all mutations to the PhoS protein result in proteins that no longer elute from a cation exchange column at the same salt concentration as the recombinant antibody. Preferably the mutant PhoS proteins will elute at less than 100 mM NaCl, whereas the antibody elutes at 200 mM at pH 4.5. More preferably the mutant PhoS proteins will not bind a cation exchange column at all at a pH of 5.0 or less. In one embodiment of the present invention the mutant PhoS proteins will bind an anion exchange column at pH8 or greater where the wild type PhoS does not.

Preferably alterations in the physical properties of, contaminating host proteins do not significantly affect the biological activity or function of the protein. In one embodiment of the present invention mutant PhoS proteins remain functional as determined by their ability to complement a PhoS deficient *E. coli* strain, ANCC75 (Amemura et al., 1982, *Journal of Bacteriology*, 152, 692-701). Preferably all mutations in *E. coli* host proteins do not affect the growth of *E. coli* or the yield of recombinant antibody compared to wild type.

The recombinant antibody produced in the *E. coli* host cells of the present invention is any immunoglobulin molecule including any antigen binding immunoglobulin fragment, such as Fv, Fab, Fab' and F(ab')$_2$ fragments, and any derivatives thereof, such as single chain Fv fragments. The production of antibodies is well known in the art and antibody fragments are routinely produced in *E. coli* by refolding from inclusion bodies or by functional expression by secretion to the bacterial periplasm (Plückthun and Pack 1997, *Immunotechnology*, 3, 83-105; Verma et al., 1998, Journal of Immunological Methods, 216, 165-181).

The purification process for a given antibody is the sequence of purification steps required to generate pure recombinant antibody following expression of said antibody in *E. coli*. The purification of recombinant antibodies is well known in the art and for each antibody a purification process can be devised which generates the maximum yield and purity using the least number of purification steps. Recombinant antibodies can be purified using one or more purification steps, examples of which include ion exchange chromatography, hydrophobic interaction chromatography, size exclusion, isoelectric focusing, Reverse Phase HPLC, chromatofocusing, SDS-PAGE, ammonium sulfate precipitation, and affinity chromatography (e.g. using protein A, protein G, or antigen as the capture reagent). The most common methods used for large-scale production of recombinant antibodies are fractional precipitation, ion exchange, hydrophobic interaction chromatography and size exclusion chromatography because these methods are cost efficient and physically robust. These methods separate proteins on the basis of their physical characteristics, isoelectric point, hydrophobicity and size respectively. If contaminating *E. coli* proteins have similar physical properties to the recombinant antibody it may not be possible to separate the proteins using these methods. For these antibodies it will be necessary to include additional more expensive purification steps such as protein-A and protein-G affinity chromatography.

From examination of the purification process for a given recombinant antibody the person skilled in the art can quickly determine whether there are contaminating *E. coli* proteins which co-purify with the recombinant antibody and are difficult to remove. The existence of such contaminating proteins will already be known to the person who has devised the purification process, for example there may be additional steps incorporated into the process solely for their removal. Alteratively, SDS-PAGE gels of column fractions will reveal which proteins consistently co-purify with the recombinant antibody.

From examining the purification process the person skilled in the art can determine which physical property or properties of said contaminating protein(s) it would be desirable to change, such that the purification of the recombinant antibody can be improved for example, by using fewer or different purification steps. For example, it may be appropriate to reduce or increase the size of the contaminating protein(s) to allow separation from the recombinant antibody using size exclusion chromatography rather than by using an expensive affinity chromatography step. Alternatively it may be appropriate to alter the isoelectric point or hydrophobicity of the contaminating protein to allow separation by ion exchange or hydrophobic interaction chromatography. A person skilled in the art can easily identify the optimal change in physical property for a contaminating protein in a given purification process. It may also be desirable to change the properties of more than one *E. coli* protein and/or more than one physical property of said proteins.

Having selected *E. coli* proteins which co-purify with the recombinant antibody and determined which physical properties of said proteins is would be desirable to change to improve the purification process, it is necessary to clone the gene encoding said proteins so that the alterations in physical properties can be made. This is routine for someone skilled in the art and first requires that protein sequence is obtained from the protein. This can be achieved for example, by N-terminal sequencing of proteins from western blots or sequencing of tryptic or CNBr fragments generated from said blots, all of which are routine methods for obtaining protein sequence. Such western blots can be generated from SDS-PAGE gels on which column fractions containing the contaminating host protein have been electrophoresed. The amino acid sequence obtained from said proteins can then be used to identify by homology searching the full protein and DNA sequence from databases such as SwissProt or Genbank given that the entire genomic sequence of *E. coli* is publicly available (Blattner et al., 1997, *Science*, 277 1453-1462). The gene encoding the contaminating protein can then be cloned using well known techniques such as PCR using primers based on the nucleic acid sequence and using *E. coli* DNA as a template.

Once the contaminating *E. coli* protein has been identified and the gene encoding said protein cloned, the gene can then be modified to generate the required physical changes in the protein that will result in improved purification of the recombinant antibody. The methods for altering the physical properties of proteins are well known in the art and many systematic changes may be required to achieve the desired result. From analysis of the protein sequence, sequence alignments and crystal structure, if available, it is possible for the person skilled in the art to identify regions of the protein that may be amenable to alteration. The regions chosen will depend on the intended changes in physical property. For example, to alter the pI or hydrophobicity of the protein it will be necessary to focus on surface exposed residues of a particular charge or hydrophobicity. Alterations in size may focus on particular domains that can be deleted or modified. Computer programs such as Rasmol or WebLab Viewer Lite are useful for viewing crystal structures of proteins enabling judicious and informed choices of which residues to change. Additional information on residues important for the activity or structure of the protein may be available in the public domain.

Preferably the protein will remain functional and examination of protein sequence alignments and crystal structures if available, should enable active site regions to be avoided. If the crystal structure is not available, identification of residues that can be altered without destroying protein function or expression can be tested using methods well known in the art such as alanine scanning mutagenesis (Cunningham and Wells, 1989, *Science*, 244, 1081-1085).

A preferred method of altering the physical properties of proteins is by the addition of protein tags, the methods for which are widely known in the art. To date these have been used to alter the properties of recombinant proteins to aid their purification rather than to alter contaminating host proteins. When these tags are used on the recombinant protein they need to be removed from the purified protein in order to restore protein function, enhance its solubility or for therapeutic purposes because the tag is antigenic. This can often present difficulties and may be the biggest impediment to the successful application of this technology (Sassenfeld, 1990, *Tibtech*, 8, 88-93). In the present invention removal of such tags is not required as the tag is used to change the pI of contaminating *E. coli* proteins rather than the recombinant antibody itself. The pI, hydrophobicity and size of proteins can all be altered by the addition of amino acid tags, the nature of which will depend on the required outcome. For example, tags appropriate is for altering the isoelectric point of a protein are poly-arginine tags (Sassenfeld and Brewer, 1984, *Biotechnology*, 2, 76-81; Brewer U.S. Pat. No. 4,532,207; Niederauer et al., 1996, *Biotechnology Progress*, 10, 237-

245; Stempfer et al., 1996, *Nature Biotechnology,* 14, 329-334), poly-glutamic acid tags (Dalbøge et al., 1987, *Bio/Technology,* 5, 1447-1457;

Niederauer et al., 1996) and bespoke protein domain tags (Gräslund et al., 2000, *Protein Engineerng,* 13, 703-709 and Gräslund et al., 2002, *Journal of Chromatography,* 942, 157-166). Tags that can be used to alter hydrophobicity include poly-phenylalanine tags (Persson et al.,1988, *Analytical Biochemistry,* 172, 330-337) and elastin-like polypeptides (Meyer and Cholkoti, 1999, *Nature Biotechnology,* 17, 1112-1115). There are also many proteins and domains of proteins that have been used as viable fusion partners which increase the size of the target protein, including alkaline phosphatase (Carrier et al., 1995, *Journal of Immunological Methods,* 181, 177-186), β-galactosidase (Nielsen et al., 1988, *JIMM* 111, 1-9), maltose binding protein (di Guan et al., 1988, *Gene,* 67, 21-30), GST (glutathione S transferase, Smith and Johnson 1988, *Gene,* 67, 31-40), cellulose binding domain (Ong et al., 1989, *Bio/Technology,* 7, 604-607), DsbA (Collins-Racie et al., 1995, *Bio/Technology,* 13, 982-987), DsbC (Novagen), thioredoxin and NusA (Novagen). Such fusions can result in an increase in size of 10-60 kDa. Such tags may be used alone or in combination with other specific alterations to the contaminating protein described below.

Another preferred method of altering the physical properties of host proteins is the modification of specific residues, the methods for which are well known in the art. For example, the electrostatic properties of a subtilisin have been modified by changing the surface charges of the subtilisin through the introduction of multiple charged amino acid residues using the X-ray crystal structure as a guide (Egmond et al., 1996, *In Subtilisin Enzymes: Practical Protein Engineering,* R Bott and C Betzel eds, 219-228). Marttila et al., 1998, *FEBS Letters,* 441, 313-317, have produced several charge mutants of avidin with pls ranging from 9.4 to 4.7, compared to the native pI of 10.5. The mutants were generated by replacing basic residues such as lysine and arginine with neutral or acidic amino acids based on known crystallographic data together with comparative sequence alignments.

Choosing which surface residues to mutate can be assisted by considering the position of the residue relative to active site, degree of solvent exposure, potential interaction with other surface residues, relative solvation potential of the amino acid R-groups involved, pKa of amino acids, relative hydrophobicity/hydrophilicity of the amino acids involved, structural and steric considerations including the relative length of the R-groups involved.

Mutations to specific residues can be achieved by methods well known in the art such as oligonucleotide-mediated mutagenesis (Zoller and Smith, 1982, *Nucleic Acid Research,* 10, 6487). To make changes to the isoelectric point of a protein it is necessary to mutate neutral amino acids to ones of the desired charge, or to change residues for ones with opposite charges (i.e. lysine/arginine for aspartic/glutamic acid. Typically to raise the pI of the protein more basic amino acids such as lysine and arginine should be incorporated into the protein, replacing acidic amino acids such as aspartic acid and glutamic acid. To decrease the pI the choice of substitutions should be reversed.

Alternatively it may be desirable to reduce the hydrophobicity of the contaminating protein and this can be achieved by replacing hydrophobic residues such as valine, leucine, isoleucine, phenylalanine, tryptophan, methionine and proline with more hydrophilic or polar residues such as serine, threonine, cysteine, tyrosine, aspartic acid, glutamic acid, asparagine, glutamine, histidine, lysine or arginine. Alternatively to increase the hydrophobicity the amino acid substitutions should be reversed.

It is also possible to reduce the size of the contaminating protein by identifying specific domains or parts of the protein that can be deleted without affecting protein expression and optionally function. These may be N or C-terminal domains or exposed loops that can be deleted to form in frame fusions. Alternatively amino acid tags or protein domains, such as those described earlier may be fused to the protein in order to increase the size of the contaminating protein to improve separation using size exclusion chromatography.

One skilled in the art will appreciate that it is difficult to predict the exact effect of the substitution, deletion, insertion or tag on the expression, activity or physical properties of the contaminating protein. The person skilled in the art will test a series of different alterations to achieve the required outcome. These may be created and tested sequentially or in parallel. One skilled in the art will appreciate that the effect may be evaluated by routine screening assays such as those described below followed by further modifications if necessary.

In order to test each mutant the altered protein must be expressed in an *E. coli* host cell that does not express the unmodified protein. This can be achieved by using an is *E. coli* host that does not express the gene, such as a deletion mutant, or by culturing said host under conditions where expression of the gene is repressed. The altered contaminating protein can be introduced by way of a plasmid, which will result in high levels of expression of said protein. Alternatively, the mutant protein can be tested by direct integration of the altered gene into the *E. coli* genome, thus replacing the endogenous gene.

The successful expression of each altered protein can be confirmed by SDS-PAGE analysis following fermentation of the *E. coli*. There may be cases where the altered protein will not express properly and these mutations should be avoided. Following successful expression of the mutated protein, the alterations in physical properties can be evaluated by chromatography and gel electrophoresis. For example if the alteration should lead to a decrease in size this can be tested on a size exclusion column and on SDS-PAGE. If the alteration should lead to a change in pI this can be tested using ion exchange chromatography and isoelectric focusing. If the alteration should lead to a change in hydrophobicity this can be tested using hydrophobic interaction chromatography and solvent solubility. It should be possible for one skilled in the art to evaluate the altered proteins by these methods in the absence of the recombinant protein. Optionally, separation from the recombinant antibody can be confirmed by spiking the extract with purified recombinant antibody before testing.

It is preferable that the biological function of the modified *E. coli* protein is retained whilst the physical properties of the protein are altered. The functionality of the mutant Pan be tested in a number of ways widely known in the art depending on the identity of the protein. For example, the mutant protein can be tested in a biological assay that demonstrates its biological activity if this is known for example, an enzyme assay. Alternatively the gene encoding the mutant protein can be used to complement an *E. coli* mutant lacking the gene of interest followed by testing biological activity or cell growth. Many of these mutants already exist or can easily be created by one skilled in the art.

Using the methods described above it will be possible for one skilled in the art to identify at least one mutant that satisfies the requirements of the improved purification process and preferably remains functional. Preferably more than one mutant will be selected at this stage in case any of the mutants have a detrimental effect on the growth of *E. coli* or yield of recombinant antibody once integrated into the genome. Integration of the chosen mutated gene(s) into the *E. coli* genome such that the wild type gene is replaced can be achieved using methods well known in the art (Hamilton et al., 1989, *Journal of Bacteriology*, 171, 4617-4622). The altered DNA sequence that is complementary to a sequence found in *E. coli* genomic DNA is included in the vector for transformation. Transformation of *E. coli* with this vector results in homologous recombination with the genome and insertion of the altered gene in place of the wild type gene.

Following replacement of the wild type gene(s) with the modified gene sequence the improved *E. coli* host cell is transformed with the desired recombinant antibody gene sequence as in the original wild type *E. coli* expression system. The *E. coli* host cell is then cultured under the same conditions as the original wild type and cell growth and yield of the recombinant antibody measured and compared to wild type. Yield of recombinant antibody can be tested using standard methods known in the art for the recombinant antibody used. For example, antibody Fab' fragments can be quantified by ELISA. Preferably no adverse effect on antibody yield or *E. coli* growth should be observed. Should adverse effects be observed one of the other selected mutations should be used or new mutations should be generated. One skilled in the art will know that these mutations can be tested systematically or in parallel.

To confirm that the altered host protein(s) no longer co-purify with the recombinant antibody, the recombinant antibody should be purified using the desired process and the presence of the altered host protein(s) monitored by for example, SDS-PAGE. The altered host protein(s) should behave as expected due to the changes in physical properties and no longer co-purify with the recombinant antibody.

The following examples are offered by way of illustration, and not by way of limitation.

EXAMPLES

Materials and Methods

DNA Manipulations

Figure 1:
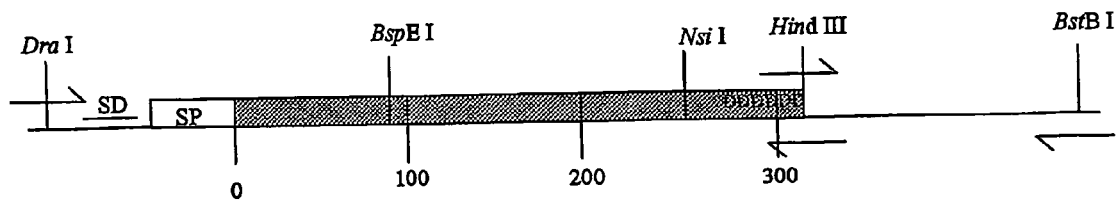
FIG. 1 Schematic plan of PCR cloning of PhoS gene

Standard methods were used for general DNA manipulations. Restriction enzymes were from Boehringer Mannheim and Taq polymerase was from Roche except for Precision Plus which was from Stratagene. Plasmid preparations were performed using Qiagen kits as per manufacturers instructions. Oligonucleotides were from Sigma-Genosys Ltd., Pampisford, U.K. The sequence of the oligonucleotide and PCR product encoded regions were confirmed by sequencing of both strands using 'PRISM Big Dye' cycle sequencing kit and an ABI PRISM-3100 sequencer using Genetic Analyzer software. The supercompetent *E. coli* strain XL1Blue MRF' Kan (Stratagene) was used for all DNA manipulations. The wild type *E. coli* W3110 (ATCC ref. 27325) were rendered competent for electroporation by washing and concentration three times in ice cold sterile 10% (v/v) glycerol for electroporation using a BioRad Gene Pulser with pulse control machine at 2000V 25 mS and 200Ω. A fresh single fresh W3110 colony was grown in 100 ml of 2xPY media at 37° C. until the $OD_{600}$ reached ~0.5-0.8. Thereafter the culture was cooled on ice for 15 minutes before pelleting the cells in ice cold centrifuge tubes at 4° C. at 4000 g for 10 minutes. The cell pellet was resuspended, washed and re-pelleted 3 times in ice cold 10% (v/v) glycerol made up in sterile de-ionised water. After the final pelleting step the cell pellet was resuspended in a final volume of 10 ml of ice cold 10% (v/v) glycerol made up in sterile de-ionised water. Cells were used immediately or frozen in liquid $N_2$ and stored at −70° C.

Bacterial Complex and Phosphate Free Media

'PhoS media' was used for all general growth of *E. coli*, plasmid preps and PhoS expression experiments in order to provide a $PO_4$ and peptide rich media to repress the pho regulon ('PhoS media'=1% (w/v) tryptone, 0.5% (w/v) yeast extract, 0.3% (w/v) $KH_2PO_4$, 0.7% (w/v) $K_2HPO_4$, 0.5% (w/v) NaCl and 0.5% (w/v) casamino acids from DIFCO). '$PO_4$ free' defined media was the MOPS media described by Neidhardt et al., 1974 Journal of Bacteriology, 119, 736-747 supplemented with glucose at 0.5% (w/v), casamino acids at 0.5% (w/v), and thiamine at 1 mM. Cells destined for integration events were grown using 2xPY (2% agar (w/v), 1% phytone, (w/v), 0.5% yeast extract (w/v), 0.5% NaCl (w/v) and made to pH 7.0 with 1M NaOH). Media were supplemented with 3% agar (w/v), carbenicillin at 200 µg/ml or chloramphenicol at 20 µg/ml IPTG at 200 µM and XP at 40 µg/ml as appropriate.

Fab' Assembly ELISA

ELISA plates were coated overnight at 4° C. with HP6045 at 2µgml⁻¹ in PBS (HP6045, a mouse IgG2a monoclonal ant-human IgG Pan Fd ($CH_1$), was obtained from hybridoma HP6045 from ATCC. Immunoglobulin was recovered from the culture supernatant by Protein A purification, and traces of bovine IgG were removed on a sheep anti-bovine IgG column). After washing 4× with $dH_2O$, serial ½ dilutions of samples and standards were performed on the plate in 100,µl of sample/conjugate buffer (100 mM Tris/Cl pH 7, 100 mM NaCl, Casein 0.2% (w/v), Tween 20 0.0002% (v/v)), and the plate shaken at 250 r.p.m., room temperature for 1 hour. After washing 4× with $dH_2O$, 100 µl of the revealing antibody GD12, HRP conjugated $F(ab')_2$ anti human kappa chains (The Binding Site, Birmingham, U.K.) was added, diluted 1/1000 in sample/conjugate buffer and the plate shaken at 200 r.p.m., room temperature for 1 hour. After washing 4× with $dH_2O$, 100 µl of 3-3'-5-5' tetramethylbenzidine (TMB) substrate was added (0.1M sodium acetate/citrate pH 6, 100 µg/ml TMB, $H_2O_2$ 0.01% (v/v)), and the $A_{630}$ recorded using an automated plate reader. The concentration of Fab' in the periplasmic extracts were calculated by comparison with purified Fab' standards of the appropriate isotype.

Cloning of PhoS Gene

The wild type PhoS gene along with ~700bp of 3' chromosomal sequence was PCR cloned using W3110 *E. coli* as a template as a Dra I-BstB I restriction fragment into pSK— (Stratagene). In order to facilitate making changes to the C-terminus of PhoS three base pair changes were made just 3' to the stop codon of the PhoS gene to incorporate a novel Hind III site (see FIG. 1 for schematic plan). After making changes to the PhoS gene and testing these changes on the chromatographic performance of the PhoS protein, final 20 gene constructs were shuttled as Sal I-BamH I fragments into pKO3 for recombination into the *E. coli* chromosome. The sequence for the PhoS gene and it's surrounding genomic sequence were found in the literature and public databases (Surin et al., 1984 and Blattner et al., 1997).

Construction of Genes Encoding Mutant PhoS Proteins

Using W3110 as a template the PhoS coding sequence along with some 3' genomic sequence was cloned in two parts by PCR using Taq polymerase. The oligonucleotides used for this are shown in Table 1. Three base pairs immediately after the stop codon were changed using PCR mutagenesis to encode a Hind III site. Hence the PhoS coding region, including any changes to the 3' of the gene could be cloned as Dra I-Hind III restriction fragments into Sma I-Hind III restricted pSK- plasmid. Changes made to the 3' end of the PhoS gene include coding regions that encode for poly(hexa) aspartic acids, and poly(hexa) aspartic acids with a K318D change.

Mutations to surface residues were performed using oligonucleotide directed mutagenic PCR using oligos (shown in Table 1) that spanned useful restriction sites as shown in FIG. 1. Hence by use of PCR and restriction cloning it is possible to construct and mix these mutations.

TABLE 1

Oligonucleotides used for construction, mutagenesis, sequencing and screening of PhoS genes.

| Type of oligo-nucleotide | Sequence of oligonucleotides | Seq id no: |
|---|---|---|
| A) PhoS cloning oligo-nucleotides | Dra I (forward)<br>GTAATTGACTGAATATCAACG | 1 |
| | Hind III (forward)<br>CTGTACTAATAAGCTTCCAGGCCGGGTACGGTGTTTTACGCC | 2 |
| | Hind III (reverse)<br>CGGCCTGGAAGCTTATTAGTACAGCGGCTTACCGCTACTGTC | 3 |
| | BstBI (reverse)<br>CCGACTCTTTCATCATCACCGGGG | 4 |
| | Poly D (reverse)<br>CGGCCTGGAAGCTTATTAATCGTCATCGTCATCGTCGTACAGCGGC<br>TTACCGCTACTGTC | 5 |
| | K/D +Poly D (reverse)<br>CGGCCTGGAAGCTTATTAATCGTCATCGTCATCGTCGTACAGCGGG<br>TCCCCGCTACTGTCTTTAATATTGGTC | 6 |
| | Null PhoS (forward)<br>CGCCGCGACCTTATCGATGAGTGCTTAATAAGTGATTGAAGAAGCA<br>AGCCTGACAGGTGCAGG | 7 |

TABLE 1-continued

Oligonucleotides used for construction, mutagenesis, sequencing and screening of PhoS genes.

| Type of oligo-nucleotide | Sequence of oligonucleotides | Seq id no: |
|---|---|---|
| B) Sequencing oligo-nucleotides | Seq 1 (forward) GCGTTCGTTCAGCGTCTGCCGGG | 8 |
| | Seq 2 (reverse) CTGCTTCGCGTAAGCATATTC | 9 |
| | Seq 3 (forward) CCAATATTAAAGACAGTAGCGG | 10 |
| | Seq 4 (reverse) CATTTTGTAATGCCGGATGCGGCG | 11 |
| | Seq 5 (forward) CTGAGCTTGCGCCTGGCTGGC | 12 |
| | Seq 6 (reverse) GCTGCCAGCAGCTCAATGGCG | 13 |
| C) Screening oligo-nucleotides | PolyD screen (forward) TACGACGATGACGATGACGATTAA | 14 |
| | PhoS stop screen (forward) GCTTAATAAGTGATTGAAGAA | 15 |
| D) Surface mutagenesis oligo-nucleotides | PhoS BspE I K107E (forward) CTGAAGTGCGGAGAACTGGTGCTGGATGGTAAAACCCTCGGCGACA TCTACCTGGGCGAAATCAAGAAGTGGGATGATGAAGCCATCGCC | 16 |
| | PhoS BspE I K107/109/110E (forward) CTGAAGTCCGGAGAACTGGTGCTGGATGGTAAAACCCTCGGCGACA TCTACCTGGGCGAAATCGAAGAATGGGATGATGAAGCCATCGGC | 17 |
| | PhoS BspE I K109E (forward) CTGAAGTCCGGAGAACTGGTGCTGGATGGTAAAACCCTCGGCGACA TCTACCTGGGCAAAATCGAAAAGTGGGATGATGAAGCCATCGCC | 18 |
| | PhoS BspE I K109/110E (forward) CTGAAGTCCGGAGAACTGGTGCTGGATGGTAAAACCCTCGGCGACA TCTACCTGGGCAAAATCGAAGAATGGGATGATGAAGCCATCGCC | 19 |
| | PhoS BspE I K110E (forward) CTGAAGTCCGGAGAACTGGTGCTGGATGGTAAAACCCTCGGCGACA TCTACCTGGGCAAAATCAAGGAATGGGATGATGAAGCCATCGCC | 20 |
| | PhoS EcoR I K275E (forward) GTGCTGGAATTCTTCGACTGGGCGTACAAAACC | 21 |
| | PhoS Nsi I K262/265/266E (forward) GAAGATGCATGGCCTATTACCTCTACCACGTTCATTCTGATCCACG AAGATCAGGAAGAACCAGAACAAGGCACAGAAGTGCTG | 22 |
| | PhoS Nsi I K262/265E (forward) GAAGATGCATGGCCTATTACCTCTACCACGTTCATTCTGATCCACG AAGATCAGGAAAAACCAGAACAAGGCACAGAAGTGCTG | 23 |
| | PhoS Nsi I K262/266E (forward) GAAGATGCATGGCCTATTACCTCTACCACGTTCATTCTGATCCACG AAGATCAGAAGGAACCAGAACAAGGCACAGAAGTGCTG | 24 |
| | PhoS Nsi I K262E (forward) GAAGATGCATGGCCTATTACCTCTACCACGTTCATTCTGATCCACG AAGATCAGAAGAACCAGAACAAGGCACAGAAGTGCTG | 25 |
| | PhoS Nsi I K265/266E (forward) GAAGATGCATGGCCTATTACCTCTACCACGTTCATTCTGATCCACA AAGATCAGGAAGAACCAGAACAAGGCACAGAAGTGCTG | 26 |
| | PhoS Nsi I K265E (forward) GAAGATGCATGGCCTATTACCTCTACCACGTTCATTCTGATCCACA AAGATCAGGAAAAACCAGAACAAGGCACAGAAGTGCTG | 27 |
| | PhoS Nsi I K266E (forward) GAAGATGCATGGCCTATTACCTCTACCACGTTCATTCTGATCCACA AAGATCAGAAGGAACCAGAACAAGGCACAGAAGTGCTG | 28 |
| | PhoS BspE I (reverse) CAGTTCTCCGGACTTCAGCCCTGGAATGTTAACCGC | 29 |
| | PhoS EcoR I K275E (reverse) GTCGAAGAATTCCAGCACTTCTGTGCCTTGTTCTGG | 30 |
| | PhoS Hind III K309/313/318E (reverse) CGATAAGCTTATTAATCGTCATCGTCATCGTCGTACAGCGGTTCAC CGCTACTGTCTTCAATATTGGTTTCCCACGCAGCGCGAACCTGTTC AAC | 31 |

Construction of Mutant PhoS Integrating Recombination Plasmids

The efficiency of directed homologous recombination of mutated genes into the *E. coli* chromosome is increased if there are flanking regions of 100% sequence identity on either side of the inserted sequence. The length of these flanking regions is usually in the order of 200-1000 bp (Hamilton et al., 1989, *Journal of Bacteriology*, 171, 4617-4622). Approximately 700 bp of chromosomal sequence 3' to the mutagenic changes was PCR cloned by virtue of an introduced Hind III site and an innate BstB I site. This Hind III-BstB I fragment was cloned into Hind III-Cla I restricted pSK-.

After construction and testing of all PhoS mutants expressed from pSK-, all final PhoS genes of interest had the 3' chromosomal flanking region described above cloned in behind it by moving the 676 bp Hind III-Xho I fragment of 3' chromosomal flanking region into similarly restricted PhoS expression plasmids. The PhoS integration cassette was moved as a 1852 bp BamH I-Sal I restriction fragment into similarly restricted pKO3 homologous recombination/replacement plasmid (Link et al., 1997, *Journal of Bacteriology*, 179, 6228-6237).

Construction of Chromosomal Replacements of PhoS Gene in W3110.

The plasmid pKO3 (Link et al., 1997) was used to generate markerless chromosomal gene replacements. The plasmid uses the temperature sensitive mutant of the pSC101 origin of replication along with a chloramphenicol marker to force and select for chromosomal integration events. The sacB gene which encodes for levansucrase is lethal to *E. coli* grown on sucrose and hence (along with the chloramphenicol marker and pSC101 origin) is used to force and select for de-integration and plasmid curing events. This methodology had been described previously (Hamilton et al., 1989, *Journal of Bacteriology*, 171, 4617-4622 and Blomfield et al., 1991, *Molecular Microbiology*, 5, 1447-1457).

Use of pKO3 Integration Plasmid—

Day 1 100 µl of *E. coli* cells were mixed with 3 µl of pKO3 DNA in a chilled BioRad electroporation cuvette before electroporation at 2500V, 25 µF and 200Ω. 900 µl of 2xPY was added immediately, the cells recovered by shaking at 250 rpm in an incubator at 30° C. for 1 hour. Cells were serially 1/10 diluted in 2xPY before 100 µl aliquots were plated out onto 2xPY agar plates containing chloramphenicol at 20 µg/ml prewarmed at 30° C. and 43° C. Plates were incubated overnight at 30° C. and 43° C.

Day 2 The number of colonies grown at 30° C. gave an estimate of the efficiency of electroporation whilst colonies that survive growth at 43° C. represent potential integration s events. Single colonies from the 43° C. plate were picked and resuspended in 10 ml of 2xPY. 100 µl of this was plated out onto 2xPY agar plates containing 5% (w/v) sucrose prewarmed to 30° C. to generate single colonies. Plates were incubated overnight at 30° C.

Day 3 Colonies here represent potential simultaneous de-integration and plasmid curing events. If the de-integration and curing events happened early on in the growth, then the bulk of the colony mass will be clonal. Single colonies were picked and replica plated onto 2xPY agar that contained either chloramphenicol at 20 µg/ml or 5% (w/v) sucrose. Plates were incubated overnight at 30° C.

Day 4 Colonies that both grow on sucrose and die on chloramphenicol represent potential chromosomal replacement and plasmid curing events. These were picked and screened by PCR with a mutation specific oligonucleotide. Colonies that generated a positive PCR band of the correct size were struck out to produce single colonies on 2xPY agar containing 5% (w/v) sucrose and the plates were incubated overnight at 30° C.

Day 5 Single colonies of PCR positive, chloramphenicol sensitive and sucrose resistant *E. coli* were used to make glycerol stocks, chemically competent cells and act as PCR templates for a PCR reaction with 5' and 3' flanking oligos to generate PCR product for direct DNA sequencing using Precision plus polymerase.

PhoS Complementation Assays

PhoS strains such as ANCC75 (Amemura et al., 1982, *Journal of Bacteriology*, 152, 692-701) constitutively express alkaline phosphatase (AP) due to a disconnection in their $PO_4$ sensing and scavenging abilities. It is possible to complement the phoS lesion with a plasmid expressed PhoS gene and complementation can be detected using chromogenic substrates for alkaline phosphatase such as 5-bromo4-chloro-3-indolyl phosphate (XP), or para-nitrophenyl phosphate (pNPP), to assay for AP activity on agar plates or in liquid media respectively. For agar plates XP was included at 40 µg/ml along with isopropyl β-D-thiogalactopyranoside (IPTG) at 200 µM and antibiotic and then colonies grown overnight at 37° C. For assay of AP in liquid media 10-100 µl samples of induced culture with an $OD_{600}$ of ~1.0 were made up to 1 ml with 1.5M Tris.Cl pH 8.0 containing 25 µl of 0.1% SDS (w/v) and 50 µl of chloroform, vortex mixed for 5 s and pre-incubated at 30° C. for 5 minutes. The assay was started by adding and mixing by inversion 200 µl of 15 mM pNPP and stopped after 10 minutes by adding and mixing by inversion 200 µl of 1M $KH_2PO_4$. The assay was performed at 30° C. After pelleting of the cells in a microfuge the absorbance of the supernatant at 420 nm was measured relative to a blank. One unit of alkaline phosphatase activity was defined as $\Delta A_{420} OD_{600}^{-1} min^{-1}$.

Theoretical MW and pI Calculations

Calculation of theoretical parameters were all done with MacVector software.

Mass Spectrometry

Molecular mass for Fab" was determined using Micromass Ultima triple quadrupole spectrometer in positive ion electrospray ionization mode. Fab" samples were desalted to remove Tris by multiple volume exchanges with 10 mM ammonium acetate using Microcon concentrators with a 10 kDa membrane cut-off size (Amicon, U.K.).

Cation Exchange Chromatography

Shake flask and fermentation cell pellets were resuspended in 100 mM Tris.Cl/10 mM EDTA pH 7.4 at 30 $OD_{600}$/ml of original culture volume respectively and agitated overnight at 30 or 60° C. After centrifugation at 4000 g for 10 minutes to remove the cell debris the supernatant was adjusted with 1M acetic acid to bring its pH down to that of the buffer in the purification experiment (typically pH4.5, 5.0 or 6.0) and then diluted with $dH_2O$ until the conductivity was $\leq 3.5$ mScm$^{-1}$. After re-checking the pH, the periplasmic extract was clarified by centrifugation at 20,000 g for 10 minutes followed by filtration through a 0.2 µm membrane.

A 5 ml SP sepharose (Pharmacia) column run in sodium acetate (NaAc) buffers was used throughout at a flow rate of 1 ml/min using a Pharmacia P500 FPLC with FPLC director software and a 10 ml sample load cylinder. The following basic elution regime was used for all PhoS and Fab" constructs: column equilibration was completed with 1 ml of equilibration buffer, 9 ml of sample was loaded and then eluted with a 70 mi (~14 column volumes) NaCl gradient from 0-200 mM in NaAc, the column was washed with 7 m 1M NaCl in NaAc and then re-equilibrated with 13 ml load buffer (NaAc). The time and conductivity of the point of elution as monitored by $A_{280}$ was noted and fractions collected manually.

Anion Exchange Chromatography

A 2.5 ml Poros HQ column (PerSeptive Biosystems) run in 20 mM Tris.Cl pH 8.0 was used throughout. Samples from cation exchange were buffer exchanged into 20 mM Tris.Cl pH 8.0 before use. Column equilibration was completed with a 1 ml wash, 9 ml of sample was loaded, followed by a 10.9 ml wash step and then eluted with 3.9 ml of 1M NaCl in 20 mM Tris.Cl pH 8.0 and then re-equilibrated with 10 ml load buffer (20 mM Tris.Cl pH 8.0).

Protein fractions were monitored by $A_{280}$ and fractions collected manually.

SDS-PAGE, Immuno Blotting and IEF Gels

SDS-PAGE gels were 4-12% NuPAGE gels from Invitrogen run in MES buffer using SeeBlue2 standards. They were either stained with Coomassie or proteins were transferred to PVDF membrane using ½ Towbin buffer. IEF gels were pH 3-10 IEF vertical slab gels from Invitrogen using Serva standards pI 3-10, stained with Coomassie. After destaining gels were scanned and/or dried between cellulose membranes.

Example 1

Review of the purification process for a Fab' antibody fragment to Identify improvements that could be made by altering host proteins.

Fab' fragments expressed in *E. coli* were routinely purified from periplasmic extracts using three chromatography steps. The first step was cation exchange at pH 4.5 during which the antibody Fab' fragment binds to the cation exchange column. The Fab' fragment was eluted from cation exchange and then run on anion exchange at pH8. The Fab' fragment does not bind anion exchange at this pH and was collected in the flow through. During this step most remaining *E. coli* proteins and endotoxin bound to the anion exchange column and were removed from the Fab' preparation. A final, hydrophobic interaction chromatography (HIC) step was required to remove a single abundant *E. coli* protein that co-purified through both ion exchange steps, as determined by SDS-PAGE.

It was apparent from reviewing this purification process that it would be desirable to remove this final HIC step as this would speed up the purification process and would result in considerable cost savings on both materials and labour. The estimated cost saving for removing this single step was 15% on a molar Fab' basis. To achieve this it would be necessary to alter the physical properties of the contaminating *E. coli* protein such that it no longer co-purified with the Fab' on ion exchange and hence the HIC step would no longer be necessary. This could be achieved by altering the pI of the protein such that it either no longer binds to the cation exchange column or elutes from that column at a different salt concentration from the Fab'. This contaminating protein was later identified as the Phosphate binding protein (PhoS/PstS) (Example 2).

Another potential improvement was identified upon examination of an SDS-PAGE gel of all proteins which bind to the cation exchange column. This revealed that there were several other abundant host proteins which had bound to the column. Removal of these proteins would significantly increase the capacity of the column for Fab' binding and would consequently lead to cost savings due reduced column sizes and speed of purification. To achieve this it would be necessary to alter the pI of the contaminating proteins such that they no longer bound to the cation exchange column. These contaminating proteins were later identified as Dipeptide binding protein (DppA), Maltose binding protein (MBP), Thioredoxin and a hypothetical 24 kDa. protein (Example 2).

Example 2

Identification of the Contaminating Proteins Selected in Example 1

A periplasmic fraction produced from a standard *E. coli* W3110 fermentation was extracted overnight at 30° C. in 100 mM Tris.Cl 10 mM EDTA pH8.0. After centrifugation the supernatant was diluted with $H_2O$ and acetic acid until its pH was ≦4.5 and its conductivity was ≦3.5 mS cm$^{-1}$. This was loaded on to a cation exchange column in the normal manner. After washing the bound proteins were eluted. The Fab' and its fragments were removed by passing the eluate down a ProteinG column twice and Protein L once and then the Fab' free eluate was concentrated with an Amicon stirred cell with 10 kDa cut-off membrane. That all Fab' related peptides had been effectively removed was demonstrated with anti-kappa and anti-CH1 immunoblotting, sandwich ELISA and HPLC. Concentrated sample was analysed using Coomassie stained 4-12% SDS-PAGE gels. Identical gels were transferred to PVDF membrane, stained with PonceauS to reveal the position of bands which were excised with a clean scalpel. Proteins were subjected to N-terminal sequencing and the results used to query SwissProt. The results are shown below.

| Protein sample | Protein identified | SwissProt |
|---|---|---|
| Band 1 | Dipeptide binding protein, DppA | P23847 |
| Band 2 | Dipeptide binding protein, DppA | P23847 |
| Band 3 | Maltose binding protein, MBP | P02928 |
| Band 4 | Phosphate binding protein, PhoS/PstS | P06128 |
| Band 5 | Hypothetical 24 kDa protein | P45390 |
|  | 2° sequence of molybdate binding protein | P37329 |
| Band 6 | Thioredoxin | P00274 |
|  | 2° sequence of hypothetical 12.5 kDa protein | P76258 |

Example 3

Creation and Testing of PhoS Proteins with C-terminal Poly-ionic Tails

Effect of C-terminal poly-ionic tails on cation exchange purification at pH 4.5

Initially 3 versions of PhoS were cloned and tested for expression in *E. coli* and cation exchange purificaton: wild type PhoS (wtPhoS), a PhoS with 6 aspartic acids at the C-terminus (PhoS polyD), and a PhoS with 6 aspartic acids at the C-terminus along with a nearby K318D mutation (PhoS K/D polyD). All three expressed well in shake flasks as judged by Coomassie staining of SDS-PAGE of the crude pH adjusted periplasmic extracts. Summary of details such as plasmid, protein name, molecular weight, estimated pI, measured pI and NaCl elution profile at pH 4.5 from cation exchange column are shown in Table 2.

The addition of the polyD tail caused the PhoS protein to elute some ~20% earlier in a salt gradient relative to the wild type protein, at 103 mM NaCl. However the desired effect of the protein not binding at all to the SP sepharose column at pH 4.5 had not been achieved. There was some evidence that the additional K318D surface mutation (which is very close to the C-terminus) had an additional benefit on the cation exchange performance above that of the polyD tag alone.

Effect of a C-terminal polyD tail on anion exchange purification at pH 8.0.

Figure 2:
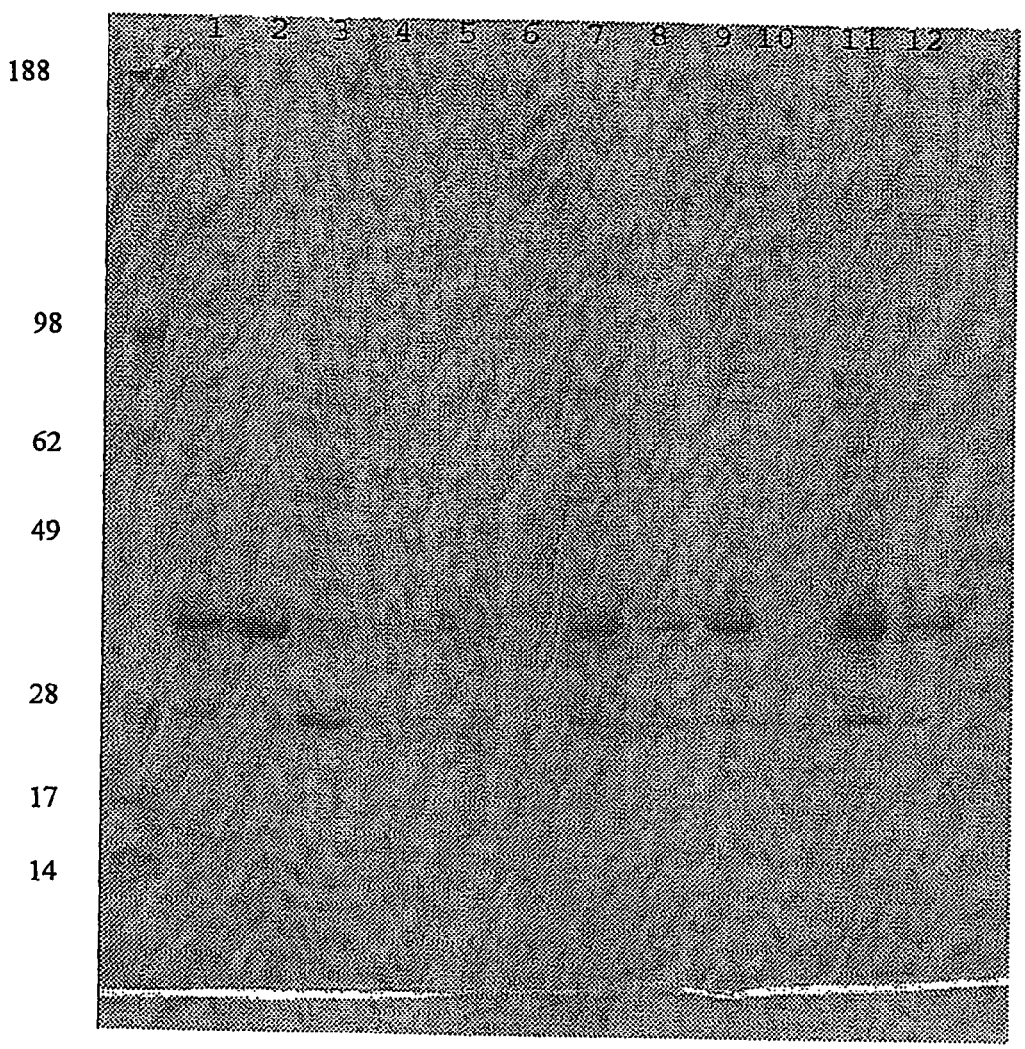
FIG. 2 Coomassie stained 4-12% SDS-PAGE of PhoS binding to anion exchange column, pH 8.0. Lanes 1-4 are wt PhoS, lanes 5-8 are PhoS polyD and lanes 9-12 are PhoS K/D polyD. Lanes 1, 5 and 9 are load, lanes 2, 6 and 10 are flow through, and lanes 3, 4, 7, 8, 11 and 12 are early and late fractions respectively of a 1M NaCl elution step.

Periplasmic extracts were simulated by pooling of flow through and elution samples from cation exchange experiments and buffer exchanged to 20 mM Tris.Cl pH 8.0. Samples for wt PhoS, PhoS polyD and PhoS K/D polyD were run on a small Poros HQ anion exchange column. The results shown in FIG. 2 show that although the wt PhoS protein does not bind to the column at this pH both the polyD and K318D polyD versions of PhoS do bind. Hence under these conditions it is likely that in addition to the pI changes that have occurred due to the presence of the polyD tag, the tag itself may be acting as an 'affinity tail' under these conditions.

TABLE 2

Details of all PhoS proteins and their plasmids

| PhoS protein | Plasmid | Protein mutations | MW (Da) theoretical | MW (Da) measured | pI calculated | pI IEF | Calculated NaCl elution from SP sepharose pH 4.5 |
|---|---|---|---|---|---|---|---|
| wt PhoS | pDPH186 | None | 34418.80 | 34422.4 ± 0.0 | 6.97 | ~7.20 | 103 mM |
| PhoS polyD | pDPH187 | C-terminal hexa-Asp tail | 35109.27 | 35112.4 ± 0.3 | 4.89 | ~5.10 | 83 mM |
| PhoS K/D poly D | pDPH188 | Hexa-Asp tail and K318D | 35096.21 | 35101.5 ± 0.3 | 4.72 | ~4.90 | 77 mM |
| PhoS K107/109/110E | pDPH191 | C-terminal hexa-Asp tail and triple K107/109/110E surface mutations | 35112.21 | ND | 4.52 | ND | Not measurable (no expression/ recovery after pH) |
| PhoS K275E | pDPH192 | C-terminal hexa-Asp tail and K275E surface mutation | 35110.24 | ND | 4.73 | ND | 100 mM (reduced expression/ recovery after pH) |
| PhoS K262/265/266E | pDPH193 | C-terminal hexa-Asp tail and K262/265/266E surface mutations | 35112.20 | ND | 4.52 | ND | 33 mM (reduced expression/ recovery after pH) |
| PhoS K309/313/318E | pDPH194 | C-terminal hexa-Asp tail and K309/313/318E surface mutations | 35114.16 | ND | 4.36 | ND | 73 mM |
| PhoS K262/265/266/ 275E | pDPH195 | C-terminal hexa-Asp tail and K262/265/266E and K275E surface mutations | 35119.06 | ND | 4.07 | ND | 55 mM (poor expression/ recovery after pH) |
| PhoS K262/265/266E, K318D | pDPH196 | C-terminal hexa-Asp tail and K262/265/266E and K318D surface mutations | 35099.15 | ND | 4.42 | ND | 46 mM (reduced expression/ recovery after pH) |
| PhoS K107E | pDPH198 | C-terminal hexa-Asp tail and K107E surface mutation | 35110.25 | ND | 4.73 | ND | 70 mM (poor expression/ recovery after pH) |
| PhoS K109E | pDPH199 | C-terminal hexa-Asp tail and K109E surface mutation | 35110.25 | ND | 4.73 | ND | 52 mM |
| PhoS K110E | pDPH200 | C-terminal hexa-Asp tail and K110E surface mutation | 35110.25 | ND | 4.73 | ND | 55 mM |
| PhoS K109/110E | pDPH201 | C-terminal hexa-Asp tail and K109/110E surface mutations | 35111.23 | ND | 4.61 | ND | Not measurable (no expression/ recovery after pH) |
| PhoS K262E | pDPH202 | C-terminal hexa-Asp tail and K262E surface mutation | 35110.25 | ND | 4.73 | ND | 68 mM |

TABLE 2-continued

Details of all PhoS proteins and their plasmids

| PhoS protein | Plasmid | Protein mutations | MW (Da) theoretical | MW (Da) measured | pI calculated | pI IEF | Calculated NaCl elution from SP sepharose pH 4.5 |
|---|---|---|---|---|---|---|---|
| PhoS K265E | pDPH203 | C-terminal hexa-Asp tail and K265E surface mutation | 35110.25 | ND | 4.73 | ND | 60 mM |
| PhoS K266E | pDPH204 | C-terminal hexa-C-terminal hexa-Asp tail and K266E surface mutation | 35110.25 | ND | 4.73 | ND | 58 mM |
| PhoS K262/265E | pDPH205 | C-terminal hexa-Asp tail and K262/265E surface mutations | 35111.22 | ND | 4.61 | ND | 57 mM (reduced expression/ recovery after pH) |
| PhoS K262/266E | pDPH206 | C-terminal hexa-Asp tail and K262/266E surface mutations | 35111.22 | ND | 4.61 | ND | 57 mM (reduced expression/ recovery after pH) |
| PhoS K265/266E | pDPH207 | C-terminal hexa-Asp tail and K265/266E surface mutations | 35111.22 | 35113 ± 0.3 | 4.61 | ~4.80 | 38 mM |
| PhoS K110E K318D | pDPH208 | C-terminal hexa-Asp tail and K110E and K318D surface mutations | 35097.20 | 35099.8 ± 0.5 | 4.61 | ~4.80 | 68 mM (reduced expression/ recovery after pH) |
| PhoS K110/265/266E | pDPH209 | C-terminal hexa-Asp tail and K110/265//266E surface mutations | 35112.20 | 35113 ± 0.5 | 4.52 | ~4.60 | 29 mM |
| PhoS K110/265/266E K318D | pDPH210 | C-terminal hexa-Asp tail and K110/265//266E and K318D surface mutations | 35099.20 | 35099.5 ± 0.3 | 4.43 | ~4.50 | 33 mM (reduced expression/ recovery after pH) |
| PhoS K265/266E K318D | pDPH211 | C-terminal hexa-Asp tail and K265/266E and K318D surface mutations | 35098.17 | 35100.5 ± 0.2 | 4.52 | ~4.60 | 52 mM (reduced expression/ recovery after pH) |

Example 4

Effect of surface mutations and a C-terminal polyD tail on the cation exchange purification of PhoS at pH 4.5.

The crystal structure of PhoS with $PO_4$ bound to the active site (Luecke and Quiocho, 1990, *Nature*, 347, 402-406) was analysed to find surface residues that were available for mutation. Lysine residues (MW 128.17 Da, pKa=10.79) were changed to glutamic acid (MW 129.12, pKa=4.07) residues in order to reduce the pI of PhoS. The swapping of basic residues for acidic ones confers a greater potential pI change per mutation (a ~0.15 pI change on PhoS) than when changing neutral residues to acidic ones (~0.07). Also, since surface exposed glutamic acid residues are likely to be highly solvated (like lysine residues) there may be less risk of causing a serious structural perturbation than when changing many of the other (non charged) surface residues to glutamic acid. It was also important to avoid residues that were implicated from previous structural or mutagenic studies to be important in $PO_4$ binding or spatially near to these residues or indeed near to the central cleft in the middle of the PhoS molecule. Preference was given to lysine residues that project very far out of the surface of the protein and lysines that were situated in or near to large groups of basic residues.

Such groups of basic residues may form a significant charge patch that can interact with a purification matrix. Hence strategic placement of one or more acidic residues may 'break up' such a patch i.e. significantly alter the net charge at such an area and hence result in large local changes in ability to interact with a purification matrix. Finally, since the C-terminus was already altered with the polyD tail which is situated at one end of the 'split rugby ball' shaped PhoS protein it was desirable to find at least some residues that were at the opposite end of PhoS protein from the C-terminus.

The following areas were identified that fitted these criteria and that could be grouped together in linear sequence to facilitate grouped PCR mutagenesis approaches.
1) Single mutation K275E sticks out of a concave surface and is very close to K272 and is near K282.
2) Triple mutation of K107, 109 and 110, K107 is near to K98 and E155, isolated K109 projects out of PhoS, and K110 is in the vicinity of K109 very close to D112, D113 and E114.
3) Triple mutation of K262, 265 and 266, K262 is distant from K265/266 but in the vicinity of K318, whilst K265 and K266 together form a 'V' and a triad with N48
4) Triple mutation of K309, 313 and 318 are all involved in a large and diffuse area with potential to be a basic surface all being adjacent to T310 and P319.

PhoS genes encoding these four mutations were constructed and tested for expression in *E. coli* and cation exchange purification performance at pH 4.5.

The single K275E mutation (pDPH192) was found to be poorly tolerated by *E. coli* and/or was precipitated after the periplasmic extract was adjusted to pH 4.5. In addition, for protein that was recovered from cells the cation exchange elution performance was not increased over that of the PhoS polyD protein.

The triple mutation at K107/109/110E gave no detectable protein after elution from cation exchange. This was due both to very poor levels of expression in *E. coli* (as shown by an induction time course) but also possibly due to precipitation whilst the periplasmic extract was adjusted to pH 4.5. However, since these mutations were the only ones that were at the opposite end of the PhoS 'rugby ball' from the polyD tail it was subsequently split into single mutations for further analysis.

The triple mutation at K262/265/266E (pDPH193) eluted from cation exchange at 33 mM NaCl. However the level of PhoS expression/recovery after cation exchange was reduced compared to the wt PhoS, hence this triple mutation was also split into all three single mutations and all combinations of double mutations for further analysis.

The triple mutation at K309/313/318E (pDPH194) had improved cation exchange elution performance relative to the PhoS polyD (73 mM vs. 83 mM NaCl respectively) and normal levels of expression, however the elution at 73 mM was not sufficiently improved over that of the K318D single mutation+polyD (pDPH188) hence no further work was performed on these triple mutations.

Both of the single K275E and K318D mutations were combined with the triple K262/265/266E mutation (pDPH195 and pDPH194 respectively) in order to investigate whether such combinations could result in additional or synergistic effects. However, both still suffered from the low protein expression/recovery seen with K262/265/266E already.

Splitting of the K107/109/110E triple mutation into three single mutations suggested that the K107E mutation was largely responsible for the deleterious effects of this triple mutation since the single K109E and K110E mutations were able to produce more protein. Both K109E (pDPH199) and K110E (pDPH200) showed improved cation exchange elution performance (52-55 mM NaCl) and better than K107E (pDPH198) at 70 mM NaCl. Hence K109 and 110E were combined (pDPH201) to test for additional/synergistic effects. However, this double K109/110E mutation could not be expressed or recovered after adjusting to pH 4.5. This suggests that the region of PhoS that K107/109/110 are in has some important structural or solvating effect where all three parties make a contribution. K110E was chosen for further combinatorial studies this mutation appeared to be better tolerated than the K109E as judged by protein recovery.

The three single K262, 265, 266E mutations all showed improved cation exchange elution performance over PhoS polyD alone: 68 mM, 60 mM and 58 mM respectively and all had good levels of protein expression. Combination of these into double mutants suggest that it is residue K262 that is critical for maintaining good protein expression levels (structure/solubility) since when combined with either K265E (pDPH205) or K266E (pDPH206) we observe reduced protein expression/recovery levels. In addition both of these double mutants do not have improved cation exchange elution performance over that of the single K265E or K266E mutants. However the double K265/266E (pDPH207) mutant has good levels of protein expression/recovery and additive effects on cation exchange elution performance, since this protein is eluted at 38 mM NaCl (compared to 60 mM and 58 mM for the single mutations alone).

Further combination mutants were made to put K265/266E together with K110E and K318D. The K110/265/266E mutant (pDPH209) was found to have improved cation exchange elution performance, eluting at 29 mM NaCl and good levels of protein expression. The K265/266E+K318D mutant (pDPH211) had both poorer cation exchange elution performance and protein expression than the K265/266E mutation alone. Finally a 'maximal' mutation construct containing four mutations in addition to the polyD tail: K110/265/266E+K318D (pDPH210) was tested. However this suffered from reduced protein recovery and did not have improved cation exchange elution performance over either K265/266E or K110/265/266E.

Hence three PhoS constructions were chosen for further analysis to represent minimal PhoS mutations with improved cation exchange elution performance: PhoS polyD, PhoS K265/266E polyD and PhoS K110/265/266E polyD. The elution of all three mutations at lower salt concentrations than the wild type PhoS should allow separation of the mutant PhoS from the Fab' by gradient or step elution from the cation exchange column. Alternatively, depending on the pI of the mutants it may be possible to prevent them binding to the cation exchange column by increasing the pH of the buffers whilst not affecting Fab' binding. Another alternative may be to rely on the anion exchange step to remove the mutated PhoS. The pIs of the mutant PhoS proteins were determined below.

Example 5

Effect of PhoS mutagenesis on protein Integrity and pI.

Figure 3:
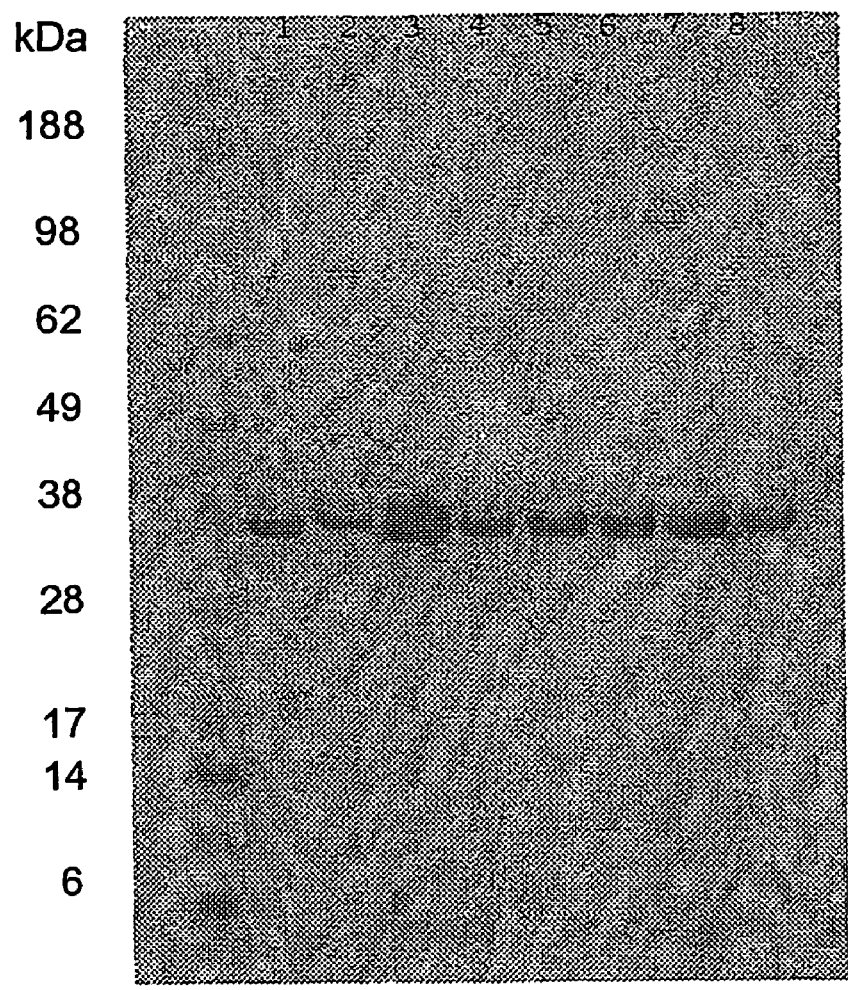
FIG. 3 Coomassie stained 4-12% SDS-PAGE of PhoS proteins purified on a NaCl gradient on SP sepharose pH 4.5. Lane 1 wt PhoS, lane 2 PhoS polyD, lane 3 PhoS K/D polyD, lane 4 PhoS K265/266E polyD, lane 5 PhoS K110E K318D polyD, lane 6 PhoS K110/265/266E polyD, lane 7 PhoS K110/265/266E K318D polyD, lane 8 PhoS K265/266E K318D polyD.
Figure 4:
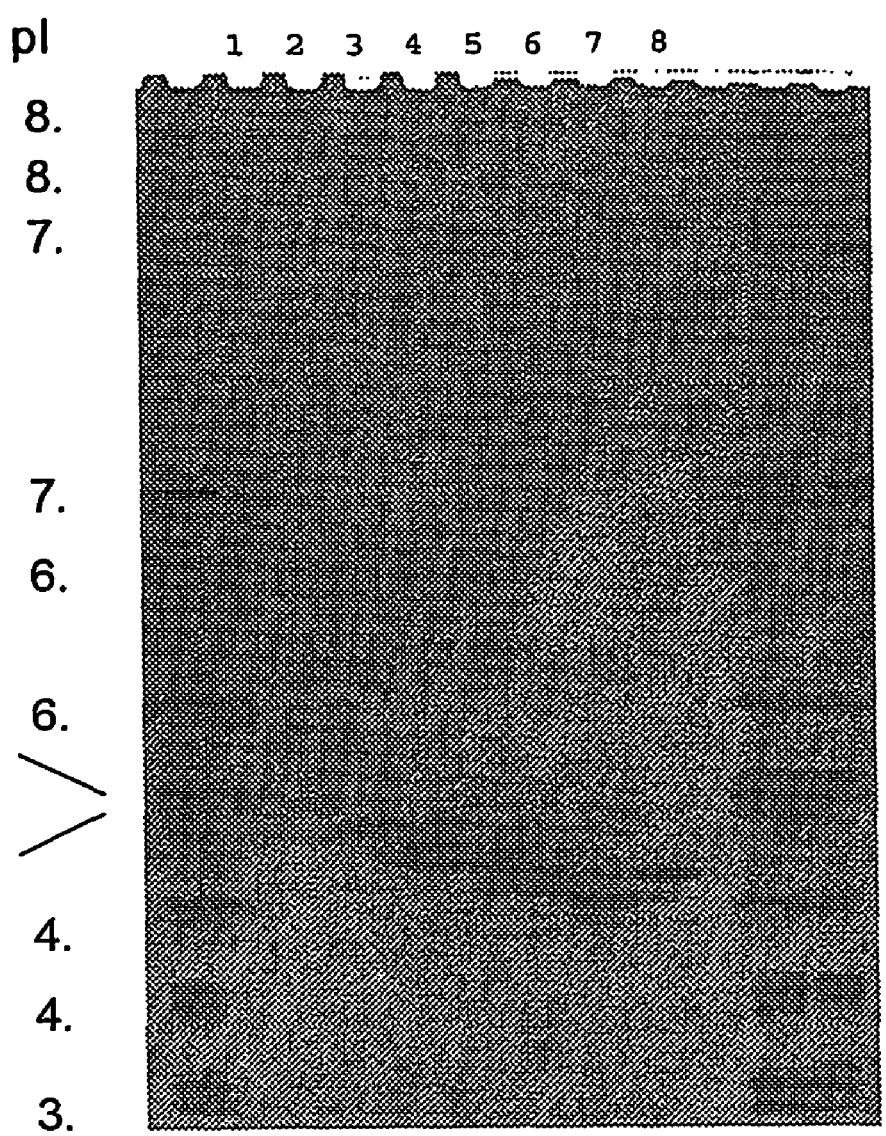
FIG. 4 Coomassie stained pH 3-10 IEF gel of PhoS proteins purified on a NaCl gradient on SP sepharose pH 4.5. Lane 1 wt PhoS, lane 2 PhoS polyD, lane 3 PhoS K/D polyD, lane 4 PhoS K265/266E polyD, lane 5 PhoS K110E K318D polyD, lane 6 PhoS K110/265/266E polyD, lane 7 PhoS K110/265/266E K318D polyD, lane 8 PhoS K265/266E K318D polyD.

Mutant PhoS proteins that were >95% pure were obtained by gradient elution cation exchange. The integrity of the protein and it's C-terminal tail was assessed by SDS-PAGE and mass spectrometry. The masses measured by MS are shown in Table 2. All show close agreement with the predicted mass both confirming that the proteins were of the correct identity and also that the polyD tail was intact. SDS-PAGE shown in FIG. 3 confirms both the level of purity of these preparations and shows a slightly slower migration for the polyD containing PhoS proteins compared to the wild type. IEF gels (FIG. 4) show that wt PhoS has a pI of ~7.2 whilst addition of the polyD tail alone reduces the pI to ~5.1. Successive additions of K to E or D surface mutations cause additional pI shifts ranging from ~4.9 for PhoS K/D polyD to ~4.8 for PhoS K265/266E polyD and ~4.5 for PhoS K110/265/266E+K318D polyD.

Example 6

Testing the functional integrity of mutant PhoS proteins: Complementation of a phoS genotype with plasmid borne PhoS.

The *E. coli* strain ANCC75 (Amemura et al., 1982) was used to provide a phoS genetic background. These cells permanently have a phenotype as if they are $PO_4$ starved and hence due to feedback through the pho regulon induce high levels of alkaline phosphatase even in the presence of $PO_4$. Growth of such cells on solid media that contains XP can distinguish between cells that have high or low levels of alkaline phosphatase. Transformation of such cells with plasmids that encode for wt PhoS, PhoS polyD, PhoS K265/266E polyD and PhoS K110/265/266E polyD or a control plasmid confirmed that all of the mutant PhoS proteins had the ability to complement the loss of the chromosomally encoded PhoS.

Figure 5:
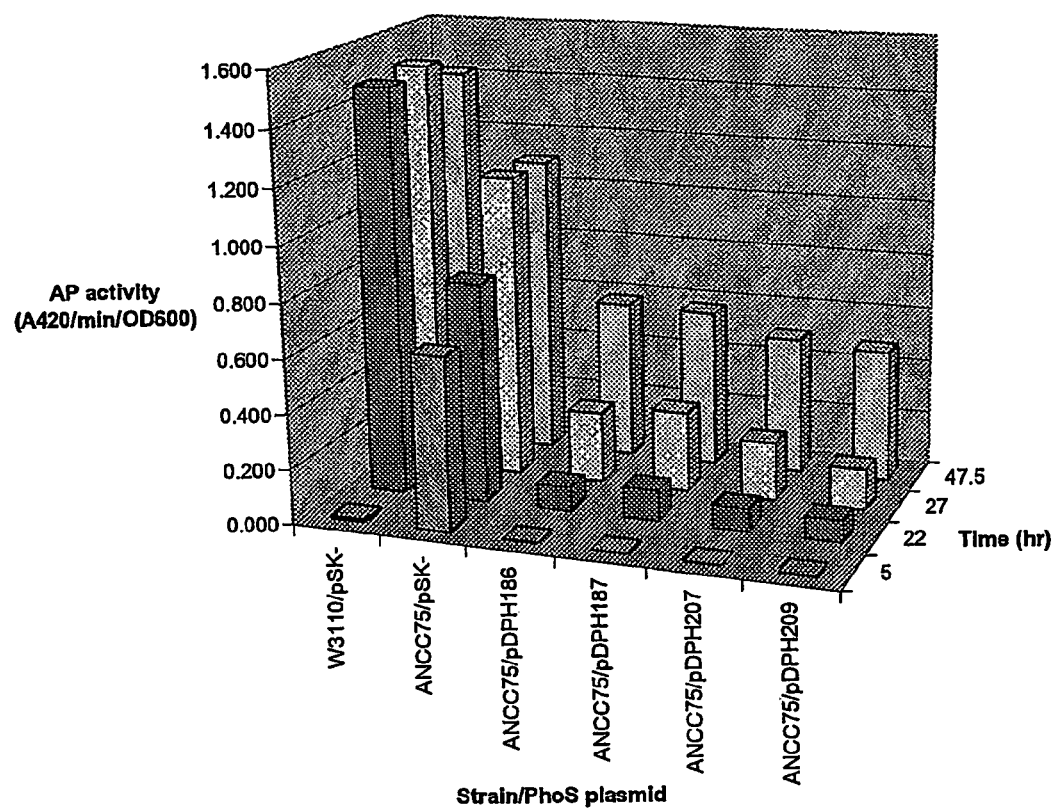
FIG. 5 Functional complementation of phoS and PO$_4$ starvation induction of alkaline phosphatase activity in a phoS and wt *E. coli* strain by plasmid encoded wt and mutant PhoS proteins.

Repeating the same experiment in liquid media that is 'phosphate free' (very low in $PO_4$) using wild type W3110 *E. coli* as a control showed (FIG. 5) that all of the mutant PhoS proteins tested were able to complement 100% the phoS phenotype under low $PO_4$ conditions (see 5 hour time point) and also partially complement the phoS phenotype under $PO_4$ free conditions (see 22, 27 and 47.5 hour time points).

Example 7

Making stable *E. coli* integrated strains expressing mutant PhoS proteins.

The genes encoding three mutant PhoS proteins (polyD, K265/266E polyD and K110/265/266E polyD) were assembled along with a length of 3' chromosomal flanking region into the chromosomal replacement plasmid pKO3. In addition a null version of PhoS was made with an oligonucleotide that had two in frame stop codons in the signal peptide coding region (plasmids pDPH217-220 respectively). These were electroporated into W3110 *E. coli* and tested for recombination and plasmid curing as described in the methods. A final PCR screen of single colonies of putative integration events using the screening oligos shown in Table I along with suitable common oligos on the opposite strand were done to test if the colonies had wild type or mutant PhoS integrated into the chromosome. PCR of chromosomal DNA (on whole *E. coli* cells) with two oligos (Dra I forward and BstB I reverse) that anneal outside of the region of DNA that was encoded in pKO3 using a high fidelity polymerase (Precision plus Taq), followed by direct sequencing of the gel purified PCR product was used to confirm that the correct changes had been incorporated into the chromosome. This resulted in production of the following four *E. coli* strains: DPH1 encodes PhoS polyD, DPH2 encodes PhoS K265/266E polyD, DPH3 encodes PhoS K110/265/266E polyD, DPH4 encodes null PhoS.

Example 8

Figure 6:
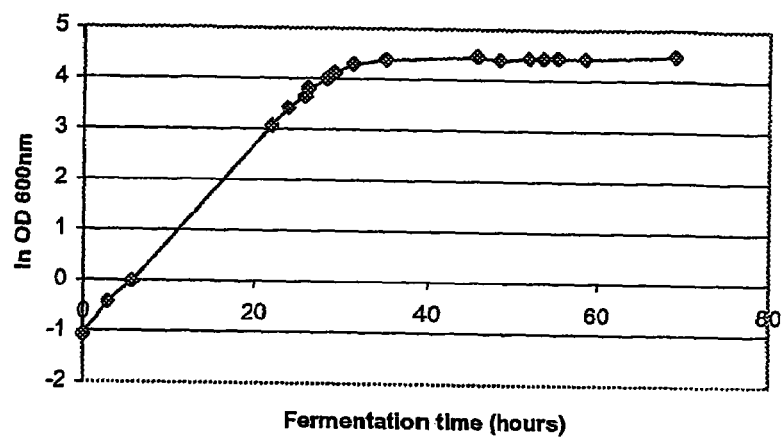
FIG. 6 Growth of DPH3 and production of Fab' by fermentation of DPH3 *E. coli*.
Figure 6:
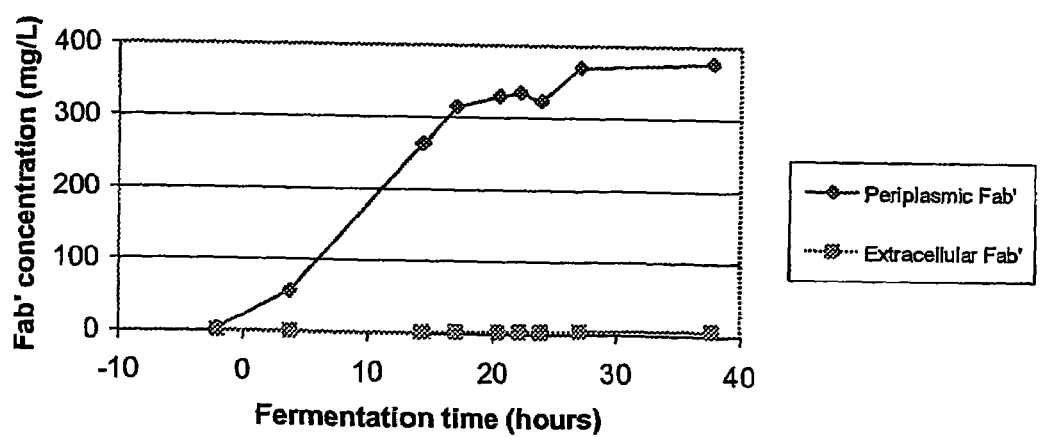

Test expression and purification of Fab' from DPH3 strain.
Strain DPH3 was transformed with a plasmid expressing the desired Fab'. A standard fermentation was performed and no obvious deficiencies or difficulties were observed during the growth or induction phase. Samples taken throughout the fermentation were assayed in the usual manner by ELISA after Tris/EDTA extraction. The data in FIG. 6 show that the growth was normal and that Fab' accumulation in the periplasm was some 380 mg/L at harvest, well within the normal range for this Fab'. Cell pellets were found to be firm and easy to resuspend after centrifugation, normally a sign of good cell integrity.

Pellets representing 50 ml of harvest culture were extracted overnight at 30° C. in Tris/EDTA then prepared for cation exchange purification as described previously. The pH was increased from 4.5 to 5.0 so that the mutant PhoS of strain DPH3 (pI 4.5) would not bind to the cation exchange column but the Fab' fragment would. The conductivity was 3.0 mS/cm. The sample was applied to a 5 ml SP sepharose column and load, flow through and elution samples analysed by Coomassie stained SDS-PAGE. Samples were concentrated where appropriate using 10 kDa cut-off spin columns to enable visualisation with Coomassie stained gels.

Figure 7:
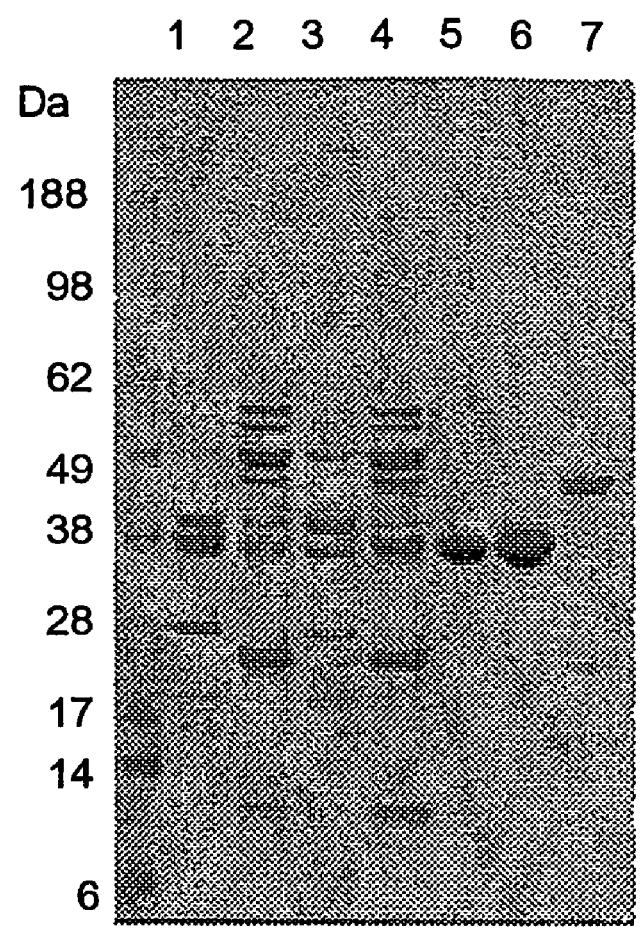
FIG. 7 Coomassie stained 4-12% SDS-PAGE of cation exchange column fractions from purification of Fab' from W3110 and DPH3 on SP sepharose at pH 5.0 and 3.0 mS/cm. Lane 1 DPH3 flow through, lane 2 DPH3 200 mM NaCl elute, lane 3 W3110 flow through, lane 4 W3110 200 mM NaCl elute, lane 5 wt PhoS, lane 6 PhoS polyD, lane 7 Fab'.

The SDS-PAGE gel in FIG. 7 shows that under these pH and conductivity conditions the mutant PhoS from DPH3 does not bind to the SP sepharose column, whilst wt PhoS from W3110 does bind. This means that for DPH3 the mutant PhoS and Fab' appear in different fractions: flow through and 200 mM NaCl elution respectively, whilst for W3110 both proteins appear in the 200 mM NaCl elution.

Figure 8:
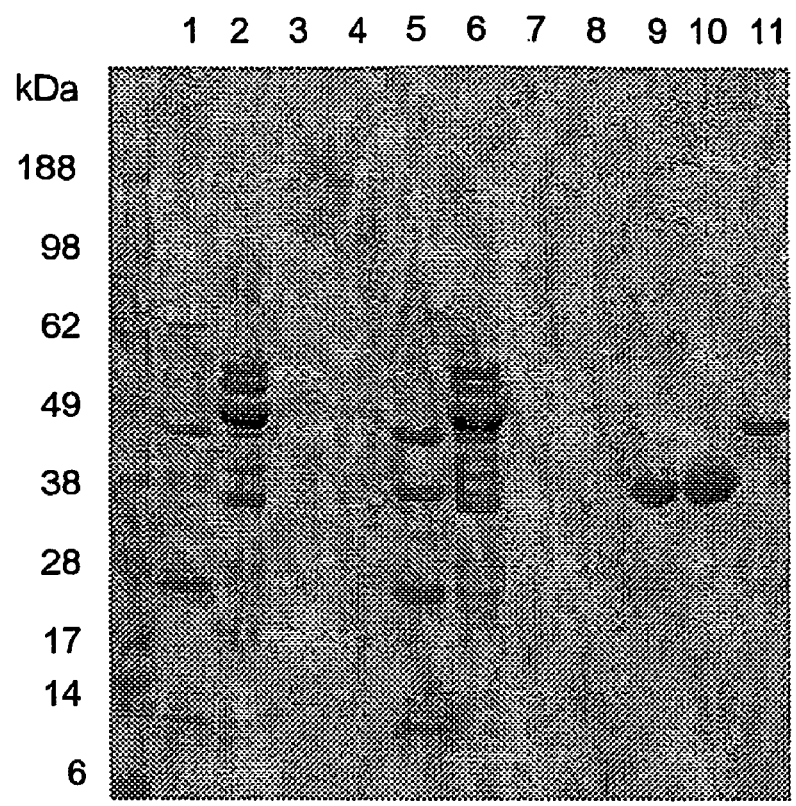
FIG. 8 Anion exchange column fractions from Poros HQ at pH 8.0 of Fab' produced in DPH3 or W3110 from cation exchange column fractions. Coomassie stained 4-12% SDS-PAGE. Eluate of DPH3 cation exchange applied to anion exchange column and collected as flow through (lane 1) or eluate (lane 2). Flow through of DPH3 cation exchange applied to anion exchange column and collected as flow through (lane 3) or eluate (lane 4). Eluate of W3110 cation exchange applied to anion exchange column and collected as flow through (lane 5) or eluate (lane 6). Flow through of W3110 cation exchange applied to anion exchange column and collected as flow through (lane 7) or eluate (lane 8). Lane 9 wt PhoS, lane 10 PhoS polyD and lane 11 Fab'.

To confirm that any remaining PhoS would also be removed by anion exchange, flow through and 200 mM NaCl elution fractions from both DPH3 and W3110 experiments were concentrated, desalted and buffer exchanged to 200 mM Tris.Cl pH 8.0 and run on anion exchange. The Coomassie stained SDS-PAGE gel shown in FIG. 8 shows that for DPH3 PhoS binds to the anion exchange column hence separating it from the Fab'. However, the wt PhoS from W3110 does not bind to the column and flows through and contaminates the Fab' solution.

Example 9

Test purification of a Fab' fragment expressed in strains DPH1, DPH2 and DPH3

Strains DPH1, DPH2 and DPH3 were transformed with a plasmid expressing a Fab' with a higher pI than the Fab' used in example 8 that is typically purified on ion exchange at pH6. A standard fermentation was performed and separation of the PhoS variants from the Fab by cation exchange chromatography was tested as described previously at pH5, 5.5 and 6.

pH5.0

Figure 9:
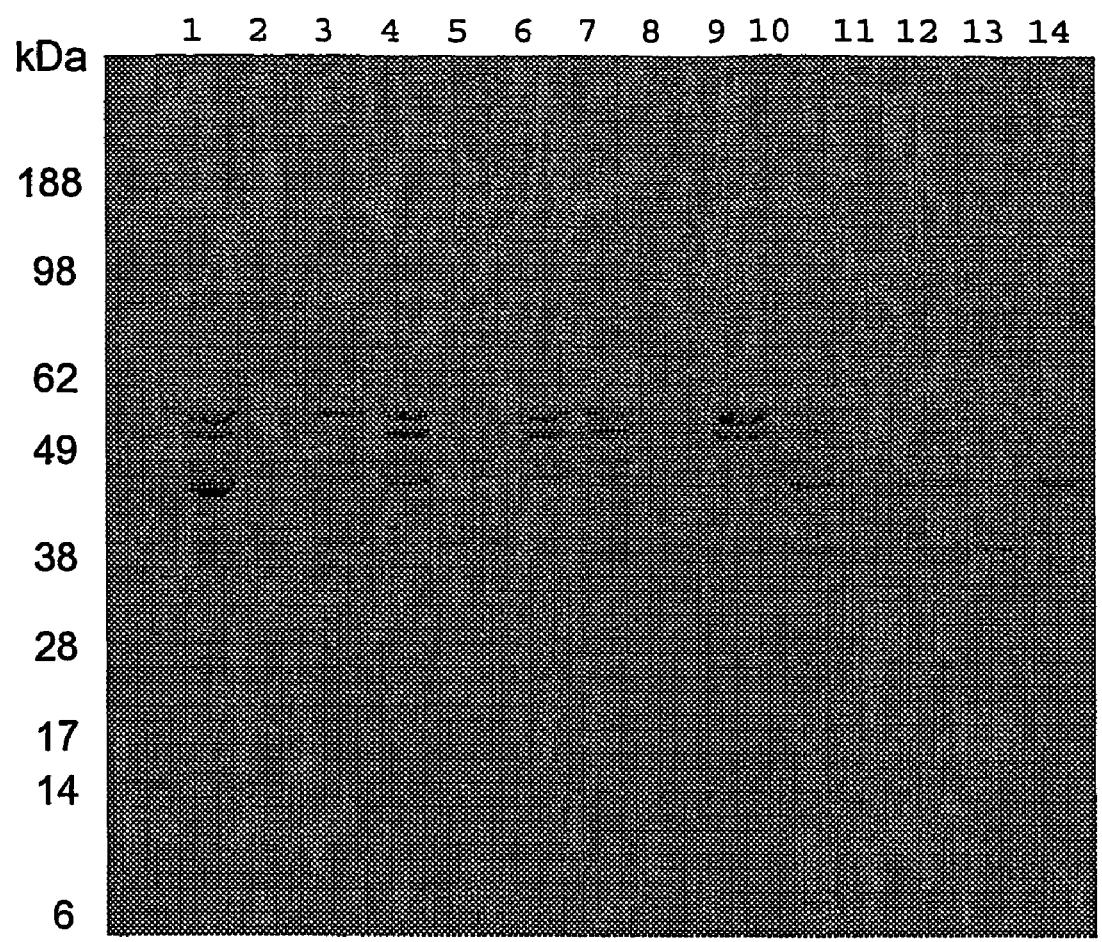
FIG. 9. Coomassie stained gel of 4-12% SDS-PAGE comparing the performance of mutant PhoS from strains DPH1, DPH2 and DPH3 during cation exchange purification of Fab'B at pH5.0. Lane 1 DPH1 load, Lane 2 DPH1 FT Lane 3 DPH1 eluate, Lane 4 DPH2 load, Lane 5 DPH2 FT, Lane 6 DPH2 eluate, Lane 7 DPH3 load, Lane 8 DPH3 FT, Lane 9 DPH3 eluate, Lane 10 W3110 load, Lane 11 W3110 FT, Lane 12 W3110 eluate, Lane 13 PhoS polyD, Lane 14 Fab'
Figure 10:
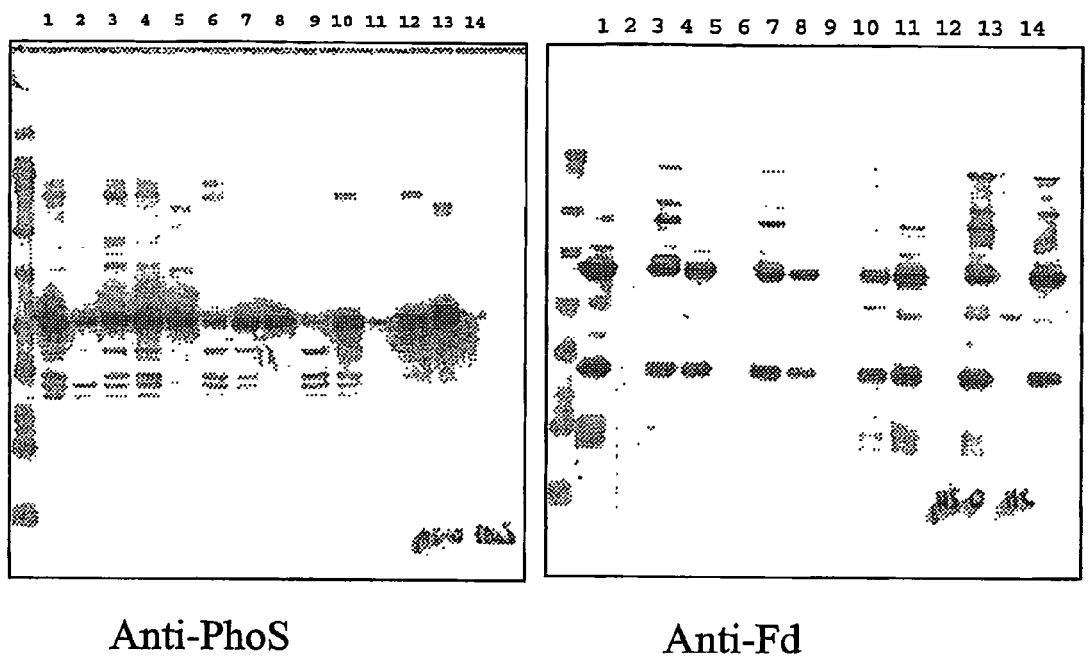
FIG. 10. Anti-PhoS and anti-Fd immunoblots of 4-12% SDS-PAGE comparing the performance of mutant PhoS from strains DPH1, DPH2 and DPH3 during cation exchange purification of Fab'-B at pH5.0.

The results for a purification done at pH5.0 are shown in FIGS. 9 and 10. At pH5 PhoS polyD (DPH1) does not appear in the flow through as judged by coomassie staining (FIG. 9, lane 2) but in fact elutes off the column with Fab'-B (FIG. 9, lane 3). The more sensitive immunoblot analysis with an anti-PhoS polyclonal and an anti-Fd monoclonal show clearly that Fab'-B binds strongly to the column along with a large amount of PhoS polyD (FIG. 10, lane 3). However the flow through fraction (lane 2) also has some PhoS polyD. This may represent that the association of PhoS polyD with the chromatography matrix is weak at pH5.0.

By contrast DPH2 which encodes for PhoS K265/266E polyD has a distinct coomassie stained PhoS band in the flow through (FIG. 9, lane 5). The anti-PhoS immunoblot shows only a trace amount of PhoS in the elute fraction (FIG. 10, lane 6). Hence PhoS K265/266E polyD effectively does not bind to SP sepharose at pH5.0.

Strain DPH3 encodes for the maximally mutated PhoS K110/265/266E polyD and again the PhoS appears in the flow through (FIG. 9, lane 8) whilst the immunoblot shows a further reduction in the amount of residual PhoS in the elute fraction (FIG. 10, lane 9) than that for DPH2 (FIG. 10, lane 6). This supports the previous observation in example 8 that the chromatographic properties of DPH3 are more capable of working at low pH (pH ~4.7-5.0) than DPH2.

The binding properties of the wild type PhoS encoded by the parent W3110 strain when loaded at pH5.0 are shown in lane 12 of FIG. 9. Anti-PhoS immunoblots show the vast majority of the wild type PhoS in the elute fraction although a trace amount can be detected in the flow through (FIG. 10, lanes 11 and 12). (The trace amounts of PhoS detected by immunoblotting in the elute fraction in these experiments may be a reflection of the minimal amount of column washing used during this rapid analytical method, whilst trace wild type PhoS in the flow through may represent weak binding to the column or a column/buffer front artifact).

pH5.5

Figure 11:
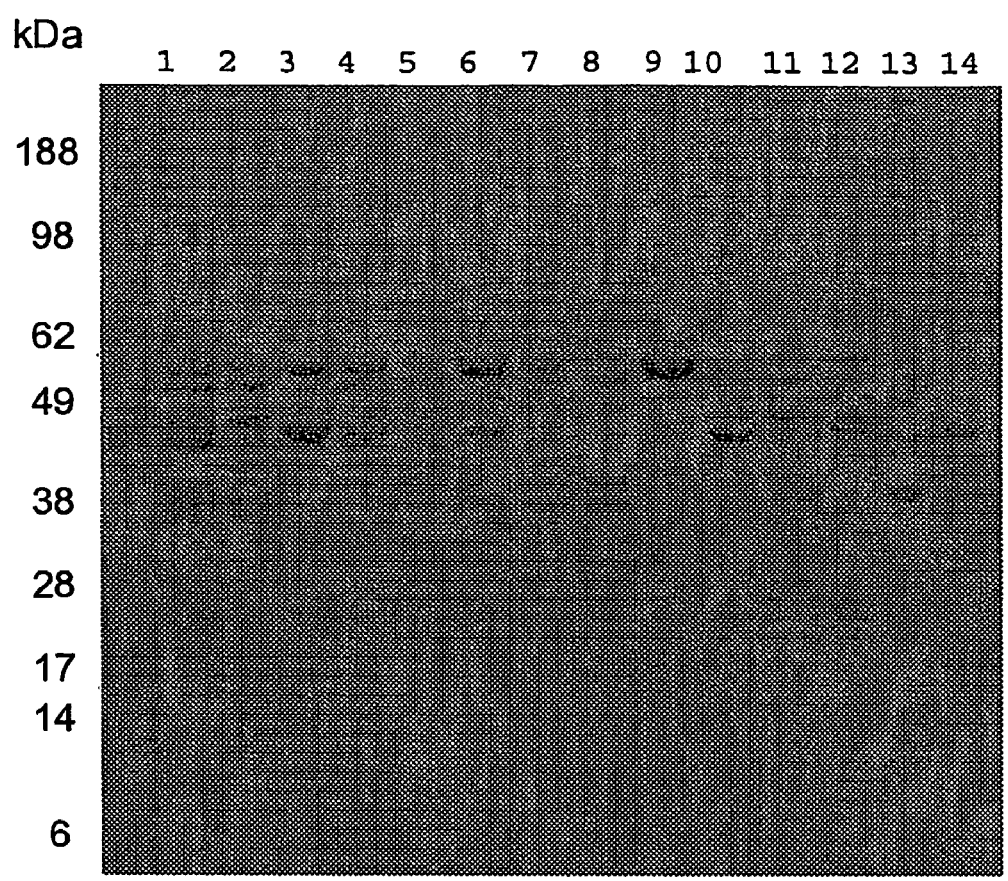
FIG. 11. Coomassie stained gel of 4-12% SDS-PAGE comparing the performance of mutant PhoS from strains DPH1, DPH2 and DPH3 during cation exchange purification of Fab'B at pH5.5.
Figure 12:
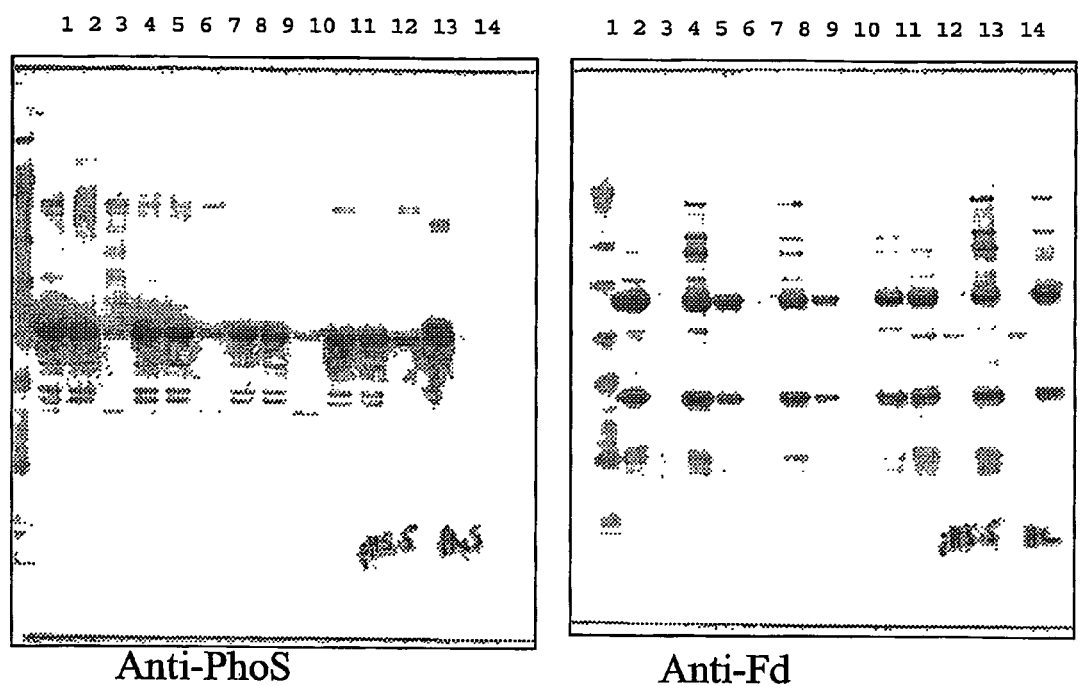
FIG. 12. Anti-PhoS and anti-Fd immunoblots of 4-12% SDS-PAGE comparing the performance of mutant PhoS from strains DPH1, DPH2 and DPH3 during cation exchange purification of Fab'-B at pH5.5.

When the three strains are analysed for PhoS purificaton at pH5.5, only the performance of DPH1 is strongly changed relative to that of pH5.0. At pH5.5 the PhoS polyD encoded by DPH1 is now found in the flow through fraction of a coomassie stained gel (FIG. 11, lane 2), which is confirmed by the anti-PhoS blot (FIG. 12, lanes 2+3). DPH2 and DPH3 encode for PhoS mutants that are in the flow through at pH5.5. The wild type PhoS encoded by W3110 has an indefinite performance. The coomassie stained gel shows that the bulk of PhoS is in the flow through at pH 5.5 (FIG. 11, lane 11), whilst the anti-PhoS blot suggests that there is still a significant portion (~40%) in the elute fraction. Hence at this pH, PhoS must be near to its functional pI and has only weak binding.

pH6.0

Figure 13:
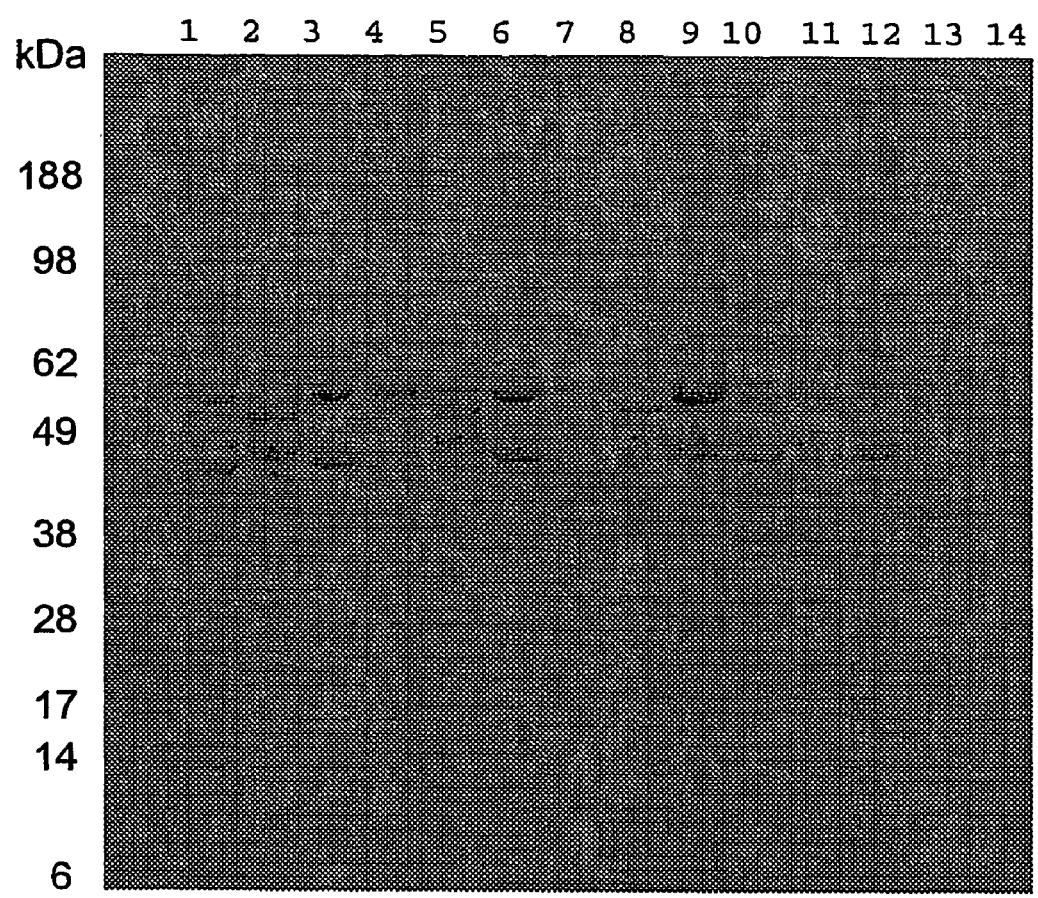
FIG. 13. Coomassie stained gel of 4-12% SDS-PAGE comparing the performance of mutant PhoS from strains DPH1, DPH2 and DPH3 during cation exchange purification of Fab'B at pH6.0

All three mutant strains and the wild type W3110 produce PhoS that does not bind to SP sepharose at pH6.0 (FIG. 13, lanes 2, 5, 8 and 11) as shown by a coomassie stained gel.

Figure 14:
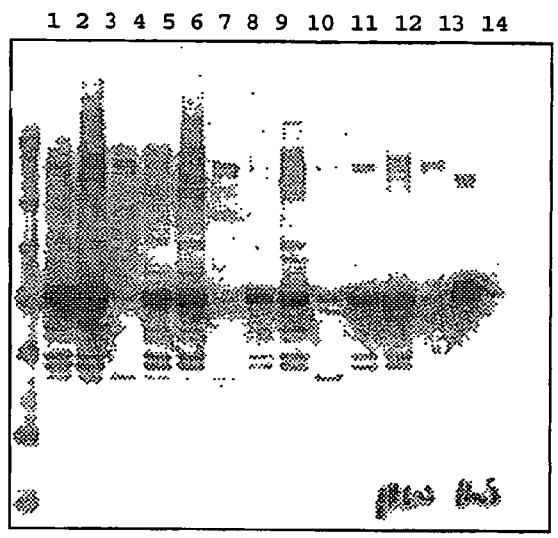
FIG. 14. Anti-PhoS and anti-Fd immunoblots of 4-12% SDS-PAGE comparing the performance of mutant PhoS from strains DPH1, DPH2 and DPH3 during cation exchange purification of Fab'-B at pH6.0
Figure 14:
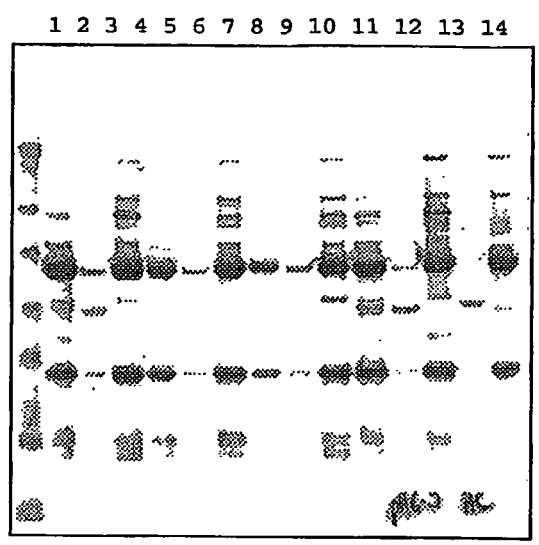

Analysis with an anti-PhoS polyclonal shows that they all have the same trace levels of detectable PhoS in the elute fraction (FIG. 14 lanes 3, 6, 9, 12). Hence there is no benefit in using strains DPH1, 2 or 3 over the wild type W3110 if cation exchange purifications are done at this pH. However, the presence of the polyD tail on the trace amounts of the PhoS in the elute fraction can make further separation of PhoS and Fab' on the second anion exchange column much easier, since the C-terminal tag effectively acts as an affinity tag when the column is operated in flow through mode.

The results summarised in Table 3, show that when tested for purification from 50 ml fermentation samples that the three ranges of PhoS mutation: PhoS polyD, PhoS K265/266E polyD and PhoS K110/265/266E polyD all have serially improved purification profiles. In these experiments, these improvements are demonstrated by the decreasing pH at which the PhoS can be found to be in the flow through of an acidified application to an SP sepharose column. Hence the proteins with the larger number of mutations can be separated from Fab' at increasingly stringent pH binding conditions. This supports the previous readout of decreased NaCl concentration required to elute these forms of PhoS off an SP sepharose column at pH4.5 (~103 mM, 83 mM, 38 mM and 29mM NaCl for W3110, DPH1, 2 and 3 respectively (Table 3)).

TABLE 3

Phos Mutant strain characteristics

| Strain | PhoS type | pI in IEF | pH for separation from Fab'-B |
|---|---|---|---|
| W3110 | wild type | 7.0 | 6.0 |
| DPH1 | PhoS polyD | 5.1 | 5.5 |
| DPH2 | PhoS K265/266E polyD | ~4.8 | 5.0 |
| DPH3 | PhoS K110/265/266E polyD | ~4.6 | 4.7-5.0 |

The invention claimed is:

1. An *E. coli* host cell expressing a recombinant antibody wherein the *E. coli* host cell has been genetically modified in order to change the isoelectric point of the *E. coli* Phosphate binding protein (PhoS/PstS) wherein the isoelectric point has been altered by: (a) the addition of a poly-aspartic acid tag to the C-terminus of the Phosphate binding protein and/or (b) changing one or more of the amino acid residues located on the surface of the *E. coli* Phosphate binding protein (PhoS/PstS) by (i) substituting one or more lysine and/or arginine residues with aspartic acid or a glutamic acid or (ii) substituting one or more aspartic acid and/or glutamic acid residues with lysine or arginine.

2. The host cell of claim 1 where the isoelectric point of the Phosphate binding protein (PhoS/PstS) has been reduced by substituting one or more lysines at residues 110, 265, 266 or 318 with glutamine or aspartic acid.

3. The host cell of claim 2 where the isoelectric point of the Phosphate binding protein (PhoS/PstS) has been reduced further by the addition of a poly-aspartic acid tag to the C-terminus.

4. The host cell of claim 1 where the isoelectric point of the Phosphate binding protein (PhoS/PstS) has been reduced by substituting the lysines at residues 265 and 266 with glutamine and by the addition of a poly-aspartic acid tag to the C-terminus.

5. The host cell of claim 1 where the isoelectric point of the Phosphate binding protein (PhoS/PstS) has been reduced by substituting the lysines at residues 110, 265 and 266 with glutamine and by the addition of a poly-aspartic acid tag to the C-terminus.

6. The host cell of claim 1 where the recombinant antibody is a Fab or a Fab' fragment.

7. A method of manufacturing a recombinant antibody which comprises fermenting a host cell according to claim 1.

* * * * *

SEQUENCE LISTING

```
<160> NUMBER OF SEQ ID NOS: 31

<210> SEQ ID NO 1
<211> LENGTH: 21
<212> TYPE: DNA
<213> ORGANISM: Escherichia coli

<400> SEQUENCE: 1
gtaattgact gaatatcaac g                                              21

<210> SEQ ID NO 2
<211> LENGTH: 42
<212> TYPE: DNA
<213> ORGANISM: Escherichia coli

<400> SEQUENCE: 2
ctgtactaat aagcttccag gccgggtacg gtgttttacg cc                       42

<210> SEQ ID NO 3
<211> LENGTH: 42
<212> TYPE: DNA
<213> ORGANISM: Escherichia coli
```

```
<400> SEQUENCE: 3
cggcctggaa gcttattagt acagcggctt accgctactg tc                          42

<210> SEQ ID NO 4
<211> LENGTH: 24
<212> TYPE: DNA
<213> ORGANISM: Escherichia coli

<400> SEQUENCE: 4
ccgactcttt catcatcacc gggg                                              24

<210> SEQ ID NO 5
<211> LENGTH: 60
<212> TYPE: DNA
<213> ORGANISM: Escherichia coli

<400> SEQUENCE: 5
cggcctggaa gcttattaat cgtcatcgtc atcgtcgtac agcggcttac cgctactgtc       60

<210> SEQ ID NO 6
<211> LENGTH: 73
<212> TYPE: DNA
<213> ORGANISM: Escherichia coli

<400> SEQUENCE: 6
cggcctggaa gcttattaat cgtcatcgtc atcgtcgtac agcgggtccc cgctactgtc       60
tttaatattg gtc                                                          73

<210> SEQ ID NO 7
<211> LENGTH: 63
<212> TYPE: DNA
<213> ORGANISM: Escherichia coli

<400> SEQUENCE: 7
cgccgcgacc ttatcgatga gtgcttaata agtgattgaa gaagcaagcc tgacaggtgc       60
agg                                                                     63

<210> SEQ ID NO 8
<211> LENGTH: 23
<212> TYPE: DNA
<213> ORGANISM: Escherichia coli

<400> SEQUENCE: 8
gcgttcgttc agcgtctgcc ggg                                               23

<210> SEQ ID NO 9
<211> LENGTH: 21
<212> TYPE: DNA
<213> ORGANISM: Escherichia coli

<400> SEQUENCE: 9
ctgcttcgcg taagcatatt c                                                 21

<210> SEQ ID NO 10
<211> LENGTH: 22
<212> TYPE: DNA
<213> ORGANISM: Escherichia coli

<400> SEQUENCE: 10
ccaatattaa agacagtagc gg                                                22
```

```
<210> SEQ ID NO 11
<211> LENGTH: 24
<212> TYPE: DNA
<213> ORGANISM: Escherichia coli

<400> SEQUENCE: 11
cattttgtaa tgccggatgc ggcg                                              24

<210> SEQ ID NO 12
<211> LENGTH: 21
<212> TYPE: DNA
<213> ORGANISM: Escherichia coli

<400> SEQUENCE: 12
ctgagcttgc gcctggctgg c                                                 21

<210> SEQ ID NO 13
<211> LENGTH: 21
<212> TYPE: DNA
<213> ORGANISM: Escherichia coli

<400> SEQUENCE: 13
gctgccagca gctcaatggc g                                                 21

<210> SEQ ID NO 14
<211> LENGTH: 24
<212> TYPE: DNA
<213> ORGANISM: Escherichia coli

<400> SEQUENCE: 14
tacgacgatg acgatgacga ttaa                                              24

<210> SEQ ID NO 15
<211> LENGTH: 21
<212> TYPE: DNA
<213> ORGANISM: Escherichia coli

<400> SEQUENCE: 15
gcttaataag tgattgaaga a                                                 21

<210> SEQ ID NO 16
<211> LENGTH: 90
<212> TYPE: DNA
<213> ORGANISM: Escherichia coli

<400> SEQUENCE: 16
ctgaagtccg gagaactggt gctggatggt aaaaccctcg gcgacatcta cctgggcgaa       60
atcaagaagt gggatgatga agccatcgcc                                        90

<210> SEQ ID NO 17
<211> LENGTH: 90
<212> TYPE: DNA
<213> ORGANISM: Escherichia coli

<400> SEQUENCE: 17
ctgaagtccg gagaactggt gctggatggt aaaaccctcg gcgacatcta cctgggcgaa       60
atcgaagaat gggatgatga agccatcgcc                                        90

<210> SEQ ID NO 18
<211> LENGTH: 90
<212> TYPE: DNA
<213> ORGANISM: Escherichia coli
```

```
<400> SEQUENCE: 18
ctgaagtccg gagaactggt gctggatggt aaaaccctcg gcgacatcta cctgggcaaa      60
atcgaaaagt gggatgatga agccatcgcc                                       90

<210> SEQ ID NO 19
<211> LENGTH: 90
<212> TYPE: DNA
<213> ORGANISM: Escherichia coli

<400> SEQUENCE: 19
ctgaagtccg gagaactggt gctggatggt aaaaccctcg gcgacatcta cctgggcaaa      60
atcgaagaat gggatgatga agccatcgcc                                       90

<210> SEQ ID NO 20
<211> LENGTH: 90
<212> TYPE: DNA
<213> ORGANISM: Escherichia coli

<400> SEQUENCE: 20
ctgaagtccg gagaactggt gctggatggt aaaaccctcg gcgacatcta cctgggcaaa      60
atcaaggaat gggatgatga agccatcgcc                                       90

<210> SEQ ID NO 21
<211> LENGTH: 33
<212> TYPE: DNA
<213> ORGANISM: Escherichia coli

<400> SEQUENCE: 21
gtgctggaat tcttcgactg ggcgtacaaa acc                                   33

<210> SEQ ID NO 22
<211> LENGTH: 84
<212> TYPE: DNA
<213> ORGANISM: Escherichia coli

<400> SEQUENCE: 22
gaagatgcat ggcctattac ctctaccacg ttcattctga tccacgaaga tcaggaagaa      60
ccagaacaag gcacagaagt gctg                                             84

<210> SEQ ID NO 23
<211> LENGTH: 84
<212> TYPE: DNA
<213> ORGANISM: Escherichia coli

<400> SEQUENCE: 23
gaagatgcat ggcctattac ctctaccacg ttcattctga tccacgaaga tcaggaaaaa      60
ccagaacaag gcacagaagt gctg                                             84

<210> SEQ ID NO 24
<211> LENGTH: 84
<212> TYPE: DNA
<213> ORGANISM: Escherichia coli

<400> SEQUENCE: 24
gaagatgcat ggcctattac ctctaccacg ttcattctga tccacgaaga tcagaaggaa      60
ccagaacaag gcacagaagt gctg                                             84
```

```
<210> SEQ ID NO 25
<211> LENGTH: 84
<212> TYPE: DNA
<213> ORGANISM: Escherichia coli

<400> SEQUENCE: 25
gaagatgcat ggcctattac ctctaccacg ttcattctga tccacgaaga tcagaagaaa      60
ccagaacaag gcacagaagt gctg                                            84

<210> SEQ ID NO 26
<211> LENGTH: 84
<212> TYPE: DNA
<213> ORGANISM: Escherichia coli

<400> SEQUENCE: 26
gaagatgcat ggcctattac ctctaccacg ttcattctga tccacaaaga tcaggaagaa      60
ccagaacaag gcacagaagt gctg                                            84

<210> SEQ ID NO 27
<211> LENGTH: 84
<212> TYPE: DNA
<213> ORGANISM: Escherichia coli

<400> SEQUENCE: 27
gaagatgcat ggcctattac ctctaccacg ttcattctga tccacaaaga tcaggaaaaa      60
ccagaacaag gcacagaagt gctg                                            84

<210> SEQ ID NO 28
<211> LENGTH: 84
<212> TYPE: DNA
<213> ORGANISM: Escherichia coli

<400> SEQUENCE: 28
gaagatgcat ggcctattac ctctaccacg ttcattctga tccacaaaga tcagaaggaa      60
ccagaacaag gcacagaagt gctg                                            84

<210> SEQ ID NO 29
<211> LENGTH: 36
<212> TYPE: DNA
<213> ORGANISM: Escherichia coli

<400> SEQUENCE: 29
cagttctccg gacttcagcc ctggaatgtt aaccgc                               36

<210> SEQ ID NO 30
<211> LENGTH: 36
<212> TYPE: DNA
<213> ORGANISM: Escherichia coli

<400> SEQUENCE: 30
gtcgaagaat tccagcactt ctgtgccttg ttctgg                               36

<210> SEQ ID NO 31
<211> LENGTH: 95
<212> TYPE: DNA
<213> ORGANISM: Escherichia coli

<400> SEQUENCE: 31
cgataagctt attaatcgtc atcgtcatcg tcgtacagcg gttcaccgct actgtcttca      60
atattggttt cccacgcagc gcgaacctgt tcaac                                95
```